(12) United States Patent
Nakamura

(10) Patent No.: US 12,419,858 B2
(45) Date of Patent: Sep. 23, 2025

(54) SALT OF TERPHENYL COMPOUND

(71) Applicant: Taiho Pharmaceutical Co., Ltd., Tokyo (JP)

(72) Inventor: Hiroyuki Nakamura, Ibaraki (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 574 days.

(21) Appl. No.: 17/775,795

(22) PCT Filed: Nov. 13, 2020

(86) PCT No.: PCT/JP2020/042383
§ 371 (c)(1),
(2) Date: May 10, 2022

(87) PCT Pub. No.: WO2021/095835
PCT Pub. Date: May 20, 2021

(65) Prior Publication Data
US 2022/0411368 A1  Dec. 29, 2022

Related U.S. Application Data

(60) Provisional application No. 62/934,923, filed on Nov. 13, 2019.

(51) Int. Cl.
*A61K 31/40* (2006.01)
*A61K 31/203* (2006.01)
(Continued)

(52) U.S. Cl.
CPC ............ *A61K 31/40* (2013.01); *A61K 31/203* (2013.01); *A61P 35/02* (2018.01); *C07D 207/14* (2013.01); *C07B 2200/13* (2013.01)

(58) Field of Classification Search
CPC .. A61K 31/40; A61K 31/203; C07B 2200/13; C07D 207/14; A61P 35/02
(Continued)

(56) References Cited

U.S. PATENT DOCUMENTS 6,225,049 B1  5/2001 Lan et al.
6,933,315 B2  8/2005 Wang et al.
(Continued)

FOREIGN PATENT DOCUMENTS

CN  107750167 B    5/2021
EP    0339006 A1 * 7/1992  ............ C07C 91/10
(Continued)

OTHER PUBLICATIONS

Korn C, Balbach S. Compound selection for development—Is salt formation the ultimate answer? Experiences with an extended concept of the "100 mg approach". European Journal of Pharmaceutical Sciences. Jun. 16, 2014;57:257-63. (Year: 2014).*

(Continued)

*Primary Examiner* — Jeffrey S Lundgren
*Assistant Examiner* — Heather Dahlin
(74) *Attorney, Agent, or Firm* — Sheppard Mullin Richter & Hampton LLP

(57) ABSTRACT

A benzoic acid salt of 4-[5-[(3S)-3-aminopyrrolidine-1-carbonyl]-2-[2-fluoro-4-(2-hydroxy-2-methyl-propyl)phenyl]phenyl]-2-fluoro-benzonitrile is provided. A sorbic acid salt of 4-[5-[(3S)-3-aminopyrrolidine-1-carbonyl]-2-[2-fluoro-4-(2-hydroxy-2-methyl-propyl)phenyl]phenyl]-2-fluoro-benzonitrile is also provided.

11 Claims, 15 Drawing Sheets

(51) Int. Cl.
    *A61P 35/02*     (2006.01)
    *C07D 207/14*     (2006.01)

(58) Field of Classification Search
    USPC .......................................................... 514/423
    See application file for complete search history.

(56) References Cited

U.S. PATENT DOCUMENTS

| | | | |
|---|---|---|---|
| 8,048,888 | B2 | 11/2011 | Wosikowski-Buters et al. |
| 8,455,477 | B2 | 6/2013 | Katz et al. |
| 9,834,521 | B2 | 12/2017 | Zech et al. |
| 10,723,742 | B2 | 7/2020 | Yamashita et al. |
| 11,510,915 | B2 * | 11/2022 | Osada ..................... A61K 31/46 |
| 2006/0110383 | A1 | 5/2006 | Honjo et al. |
| 2012/0142028 | A1 | 6/2012 | Richardson et al. |
| 2013/0035377 | A1 | 2/2013 | Minucci et al. |
| 2013/0231342 | A1 | 9/2013 | Munoz et al. |
| 2014/0105893 | A1 | 4/2014 | Kobunai et al. |
| 2015/0025054 | A1 | 1/2015 | Ortega Muñoz et al. |
| 2015/0065737 | A1 | 3/2015 | Xue et al. |
| 2016/0257662 | A1 | 9/2016 | Mccall et al. |
| 2016/0303124 | A1 | 10/2016 | Webster et al. |
| 2018/0354960 | A1 | 12/2018 | Yamashita et al. |
| 2019/0030018 | A1 | 1/2019 | Buchholz et al. |
| 2020/0190175 | A1 | 6/2020 | Hatanaka |
| 2021/0177826 | A1 | 6/2021 | Osada |
| 2021/0179634 | A1 | 6/2021 | Yamashita et al. |

FOREIGN PATENT DOCUMENTS

| | | |
|---|---|---|
| JP | 2012-506238 A | 3/2012 |
| JP | 2012-524280 A | 10/2012 |
| JP | 2013-525318 A | 6/2013 |
| JP | 2013-535460 A | 9/2013 |
| JP | 2016-531121 A | 10/2016 |
| JP | 2016-536334 A | 11/2016 |
| JP | 2017-503024 A | 1/2017 |
| RU | 2681211 C2 | 3/2019 |
| WO | WO2004/004771 A1 | 1/2004 |
| WO | WO2010/048123 A2 | 4/2010 |
| WO | WO2010/077624 A1 | 7/2010 |
| WO | WO2014/151761 A1 | 9/2014 |
| WO | WO2015/089192 A1 | 6/2015 |
| WO | WO2015/103060 A1 | 7/2015 |
| WO | WO2015/168466 A1 | 11/2015 |
| WO | WO2016/007727 A1 | 1/2016 |
| WO | WO2016/029262 A1 | 3/2016 |
| WO | WO2016/037005 A1 | 3/2016 |
| WO | WO2017/013061 A1 | 1/2017 |
| WO | WO2017/090756 A1 | 6/2017 |
| WO | WO-2018/136961 A1 | 7/2018 |
| WO | WO2018/216795 A1 | 11/2018 |
| WO | WO2018/216800 A1 | 11/2018 |
| WO | WO2018/221555 A1 | 12/2018 |
| WO | WO-2019/075327 A1 | 4/2019 |
| WO | WO2019083971 A1 | 5/2019 |
| WO | WO2019104381 A1 | 6/2019 |
| WO | WO-2019/136016 A1 | 7/2019 |
| WO | WO2021/009514 A1 | 1/2021 |
| WO | WO2021095835 A1 | 5/2021 |
| WO | 2021/178807 A1 | 9/2021 |

OTHER PUBLICATIONS

He Y, Orton E, Yang D. The selection of a pharmaceutical salt—the effect of the acidity of the counterion on its solubility and potential biopharmaceutical performance. Journal of Pharmaceutical Sciences. Jan. 1, 2018;107(1):419-25. (Year: 2018).*

Sandberg A, Abrahamsson B, Regårdh CG. Pharmacokinetics of metoprolol enantiomers after administration of the racemate and the S-enantiomer as oral solutions and extended release tablets. Drug Investigation. Dec. 1993;6:320-9. (Year: 1993).*

Caira, Mino R., "Crystalline Polymorphism of Organic Compounds", Topics in Current Chemistry, vol. 198, pp. 163-208 (1998).

Variankaval, Narayan et al., "From form to function: Crystallization of active pharmaceutical ingredients", AIChE Journal, vol. 54, No. 7, pp. 1682-1688 (2008).

Kummerer, Klaus, "Pharmaceuticals in the environment," Annual Review of Environment and Resources, vol. 35, pp. 57-75 (2010).

Bernstein, Joel, "Polymorphism of Molecular Crystals", Materials Science, pp. 324-330 (2002).

Zakharova, N. M. et al., "The Physiological significance of proliferative and alterative processes," Uspekhi Fiziologicheskikh Nauk, vol. 44, No. 3, pp. 33-53 (2013).

The Small Medical Encyclopedia, Moscow: Meditsina, vol. 5, pp. 90-96 (1996).

Official Action dated May 10, 2023 for Russian Patent Application No. 2022115757.

International Search Report and Written Opinion for International Application No. PCT/JP2018/020101, mailed Aug. 14, 2018, 28 pages.

International Search Report and Written Opinion for International Application No. PCT/JP2018/020158, mailed Jul. 17, 2018, 20 pages.

International Search Report and Written Opinion for International Application No. PCT/JP2018/020667, mailed Aug. 21, 2018, 18 pages.

International Search Report and Written Opinion for International Application No. PCT/JP2020/042410, mailed Jan. 19, 2021, 10 pages.

Amente et al., "The histone LSD1 demethylase in stemness and cancer", Biochimica et Biophysica Acta, 2013, vol. 1829, No. 10, pp. 981-986 transcription programs.

Breslin et al., "Neuroendocrine differentiation factor, IA-1, is a trascriptional repressor and contains a specific DNA-binding domain: identification of consensus IA-1 binding sequence", Nucleic Acids Research, 2002, vol. 30, No. 4.

Cannon, "Analog Design", Chapter Nineteen in Burger's Medicinal Chemistry and Drug Discovery, 5th ed., vol. 1: Pronciples and Practice, 1995, pp. 783-802.

Chen et al., "Lysine-specific histone demethylase 1 (LSD1): A potential molecular target for tumor therapy", Crit. Rev. Eukaryot. Gene Expr, 22(1): 53-59, 2012.

ClinicalTrials.gov Identifier: NCT02177812, Jun. 8, 2019, Retrieved from the internet:<URL:https://clinicaltrials.gov/ct2/show/study/NCT02177812>.

ClinicalTrials.gov Identifier: NCT02959437, Nov. 9, 2016, Retrieved from the Internet:<URL:http://www.clinicaltrials.gov/ct2/show/NCT02959437>[retrieved on Jan. 4, 2021].

ClinicalTrials.gov Identifier: NCT03132324, Apr. 27, 2017, Retrieved from the internet <URL:https://clinicaltrials.gov/ct2/show/study/NCT03132324>.

Crombie et al., "Synthesis and evaluation of azabicyclo [3.2.1]octane derivatives as potent mixed vasopressin antagonists", Bioorganic & Medicinal Chemistry Letters, 20(12), pp. 3742-3745.

Database EMBASE on STN, AN 0050300062, DN 70306324, Haematologica, 2010, vol. 95, Supp. SUPPL. 2. pp. 58. Abstract No. 0143.

Extended European search report dated Jan. 27, 2021 for EP Pat. Appl. 18809220.9.

Fang et al., "LSD1/KDM1A inhibitors in clinical trials: advances and prospects", J. Hematol. Oncol., 2019, 12: 129.

First Examination Report dated Jul. 29, 2019 for the corresponding IN patent application No. 201817022113.

Fiskus et al., Highly effective combination of LSD1 (KDM1A) antagonist and pan-histone deacetylase inhibitor against human AML cells, Leukemia, 2014, vol. 28, No. 11, pp. 2155-2164.

Harris et al., "The Histone Demethylase KDM1A Sustains the Oncogenic Potential of MLL-AF9 Leukemia Stem Cells", Cancer Cell, 2012, vol. 21, No. 4, pp. 473-487.

Hill et al., "Inhibition of LSD1 reduces herpesvirus infection, shedding, and recurrence by promoting epigenetic suppression of viral genomes", Science Translational Medicine, 2014, vol. 6, No. 265ra169.

(56) References Cited

OTHER PUBLICATIONS

Hollebecque et al., Phase I study of CC-90011 in patients with advanced solid tumours (STs) and relapsed/refractory non-hodgkin lymphoma (R/R NHL), Annals of Oncology, vol. 30, Issue Supplement_5, 2019, mdz256.003, https://doi.org/10.1093/annonc/mdz256.003.
Japanese Journal of Clinical Medicine, Recent Advances Science and Care of Leukemia (II), 74(extra No. 10 (1112)), 2016, pp. 100-104.
Kawagishi et al., "TPC-144, a novel reversible LSD1 inhibitor, exhibited strong antitumor activity in preclinical model of MAL and SCLC", The European Journal of Cancer, 2016, vol. 68, Suppelment 1, pp. S86-S87, 258.
Kholodov et al., Clinical Pharmacokinetics, 1985, pp. 83-98, 134-138, 160, 378-380.
Lan et al., "IA-1, a New Marker for Neuroendocrine Differentiation in Human Lung Cancer Cell Lines", Cancer Research, 1993, 53(18), 4169-4171.
Lan et al., "Structure, expression, and biological function of INSM1 transcription factor in neuroendocrine differentiation", FASEB Journal, 2009, 23(7): 2024-2033.
Lin et al., "Requirement of the Histone Demethylase LSD1 in Snail-mediated Transcriptoinal Repression during Eputhelical-Mesenchymal Transition", Oncogene, 2010, 29(35): 4896-4904.
Lynch et al., "LSD1 inhibition: a therapeutic strategy in cancer?", Expert Opinin on Therapeutic Targets, 2012, 16:12, pp. 1239-1249.
Maes et al., "KDM1 histone lysine demethylases as targets for treatments of oncological and neurodegenerative disease", Epigenomics, 2015, vol. 7, No. 4, pp. 609-626.
Maiques-Diaz et al., "LSD1: biologic roles and therapeutic targeting", Epigenobics, 2016, 8(8), pp. 1103-1116.
Majello et al., "Expanding the Role of the Histone Lysine-Specific Demethylase LSD1 in Cancer", Cancers (Basel), 2019, 11, 324.
Mohammad et al., A DNA Hypomethylation Signature Predicts Antitumor Activity of LSD1 Inhibitors in SCLC, Cancer Cell, 2015, vol. 28, No. 1, pp. 57-59.
Official Action dated Dec. 2, 2021 for U.S. Appl. No. 16/616,826.
Official Action dated Dec. 8, 2021 for RU Pat. Appln. No. 2019144056.
Official Action dated Apr. 21, 2020 for the corresponding RU Patent Application No. 2019144056.
Rosenbaum, "A Novel Immunohistochemical and Molecular Maker for Neuroendocrine and Neuroepithelial Neoplasms", American Journal of Clinical Pathology, 2015, vol. 144, No. 4, pp. 579-591.
Russo et al., "All-trans retinoic acid (ATRA) in patients with chronic myeloid leukemia in the chronic phase", Leukemia, 1998, 12, pp. 449-454.
Saleque et al., "Epigenetic Regulation of Hematopoietic Differentiation by Gfi-1 and Gfi-1b is Mediated by the Cofactors CoREST and LSD1", Molecular Cell, 2007, 27(49), 562-572.
Santa Cruz Biotechnology Inc., INSM1 (A-8): sc-271408, 2015.
Sergeev, "Short Course of Molecular Pharmacology", 1975, p. 10.
Shi et al., "Lysine-specific demethylase 1 is a therapeutic target for fetal hemoglobin induction", Nature Medicine, 2013, vol. 19, No. 3, pp. 291-294.
Simone, Oncology: Introduction, Cecil Textbook of Medicine, 20th Ed., 1996, vol. 1, pp. 1004-1010.
Singh et al., Inhibition of LSD1 sensitizes glioblastoma cells to histone deacetylase inhibitors, Neuro-Oncology, 2011, vol. 13, No. 8, pp. 894-903.
Somervaille et al., Safety, Phamacokinetics (PK), Pharmacodynamics (PD) and Preliminary Activity in Acute Leukemia of Ory-1001, a First-in-Class Inhibitor of Lysine-Specific Histone Demethylase 1A (LSD1/KDM1A): Initial Results from a First-in Human Phase 1 Study, Blood, 2016, 128 (22): 4060.
Sundaresan et al., "Towards a general model for protein-substrate stereoselectivity", Protein Science, 2002, 11:1330-1339.
Takagi, "LSD1 Inhibitor T-3775440 Inhibits SCLC Cell Proliferation by Disrupting LSD1 Interactions with SNAG Domain Proteins INSM1 and GFI1B", Cancer Research, 2017, vol. 77, No. 17, pp. 4652-4662.

Topalian et al., "Safety, Activity, and Immune Correlates of Anti-PD-1 Antibody in Cancer", N. Engl. J. Med., 2012, vol. 366, No. 26, pp. 2443-2454.
Venkatesh et al., "Role of the Development Scientist in Compound Lead Selection and Optimization", Journal of Pharmaceutical Sciences, vol. 89, No. 2, 2000, pp. 145-154.
Wang et al., "Identification of an INSMI-binding site in the insulin promoter: negative regulation of the insulin gene transcription", J. Endocrinol 2008, 198(1), pp. 29-39.
Welcker et al., "Insm1 controls development of pituitary endocrine cells and requires a SNAG domain for function and for recruitment of histone-modifying factors", Development, 2013, 140(24), 4947-4958.
Wu et al., 3-(Piperidin-4-ylemthoxy)pyridine Containing Compounds are Potent Inhibitors of lysine Specific Demethylase 1, Journal of Medicinal Chemistry, 2016, vol. 59, No. 1, pp. 253-263.
Ye et al., "The LSD1 inhibitor INCB059872 is synergistic with ATRA in models of non-APL acute myelogenous leukemia", Cancer Research 76 (14 Suppl), Abstract 4696, 2016.
Zhang et al., "Targeting LSD1 for acute myeloid leukemia (AML) treatment", Pharmacol. Res, 164, 2021, 105335.
International Search Report and Written Opinion for International Application No. PCT/JP2020/042383, mailed Dec. 22, 2020, 6 pages.
Restriction Requirement, dated Nov. 25, 2022, regarding U.S. Appl. No. 16/617,866, 8 pages.
Official Action dated Jul. 23, 2024 for Russian Patent Application No. 2022115757, with English translation.
Sarma et al., "Solid forms of pharmaceuticals: Polymorphs, salts and cocrystals", Korean J. Chem. Eng., 2011, 28(2), pp. 315-322.
Rodríguez-Spong et al., "General principles of pharmaceutical solid polymorphism: a supramolecular perspective", Advanced Drug Delivery Reviews, 2004, 56, pp. 241-274.
Aaltonen et al., "Solid form screening—A review", European Journal of Pharmaceutics and Biopharmaceutics, 2009, 71, pp. 23-37.
Hilfker et al., "Relevance of Solid-State Properties for Pharmaceutical Products", 2006, pp. 1-19.
International Search Report and Written Opinion, dated Nov. 15, 2022, regarding International Application No. PCT/JP2022/036343, 9 pages.
Office Action dated Mar. 23, 2023 for U.S. Appl. No. 16/617,866.
Mashkovsky, M.D., "Drugs", Moscow, "Medicine", Part 1, p. 8 (1993).
Chemical Encyclopedic Dictionary, Moscow, "Soviet encyclopedia", pp. 130-131 (1983).
Bastin, Richard J. et al., "Salt selection and Optimization Procedures for Pharmaceutical New Chemical Entities" Organic Process Research & Development, vol. 4, pp. 427-435 (DOI: 10.1021/op000018u) (2000).
Official Action dated Apr. 17, 2023 for Russian Patent Application No. 2022115555.
Lustberg, "Management of Neutropenia in Cancer Patients", Clinical advances in hematology & oncology, pp. 825-826 (2012).
Kuter, "Managing Thrombocytopenia Associated with Cancer Chemotherapy", Oncolgy, vol. 29, No. 4, pp. 1-20 (2015).
Extended European Search Report dated May 23, 2023 for European Patent Application No. 20886658.2.
Office Action, dated Jul. 23, 2024, regarding TW Application No. 111137061.
Osada et al., "Combination of TPC-144, a reversible LSD1 inhibitor, and a hypomethylating agent resulted in synergistic anti-tumor efficacy in preclinical models of AML", 2017, [Poster 169], AACR-NCI-EORTC International Conference.
Osada et al., "Combination of TPC-144, a reversible LSD1 inhibitor, and a hypomethylating agent resulted in synergistic anti-tumor efficacy in preclinical models of AML", 2017, [Abstract A169], AACR-NCI-EORTC International Conference.
Hatanaka et al., "TAS1440 (TPC-144), a novel reversible LSD1 inhibitor, exhibited strong antitumor activity in preclinical models of AML and SCLC", 2020, [Slides W5-1], The 24th Annual Meeting of Japanese Assosiation for Molecular Target Therapy of Cancer (attached program with machine translation).

(56) References Cited

OTHER PUBLICATIONS

Hatanaka et al., "TAS1440 (TPC-144), a novel reversible LSD1 inhibitor, exhibited strong antitumor activity in preclinical models of AML and SCLC", 2020, [Slides W5-1], The 24th Annual Meeting of Japanese Assosiation for Molecular Target Therapy of Cancer (Abstract).
Shibutani et al., "TAS1440, a novel reversible LSD1 inhibitor, modulates immunosuppressive population and potentiates the anti-tumor efficacy of anti-PD-1 antibody therapy", 2022, [Program and Poster 204], The 34th EORTC-NCI-AACR Symposium (attached program).
Gong et al., "Inhibition of SCLC Cell Proliferation by LSD1 Inhibitor TAS1440 through Dissociation of LSD1-INSM1 Interaction", 2023, [Poster 1P-459] of The 46th Annual Meeting of the Molecular Biology Society of Japan (attached program).
Gong et al., "Inhibition of SCLC Cell Proliferation by LSD1 Inhibitor TAS1440 through Dissociation of LSD1-INSM1 Interaction", 2023, [Poster 1P-459] of The 46th Annual Meeting of the Molecular Biology Society of Japan (Abstract).
Tanaka et al., "Role of LSD1 complex and development of new LSD1 inhibitors in neuroendocrine small-cell lung cancer", 2024, [Slides 3S07a-07], The 97th Annual Meeting of the Japanese Biochemical Society.
Tanaka et al., "Role of LSD1 complex and development of new LSD1 inhibitors in neuroendocrine small-cell lung cancer", 2024, [Slides 3S07a-07], The 97th Annual Meeting of the Japanese Biochemical Society (Abstract).
Gong et al., "TAS1440, an LSD1 Inhibitor, Exhibits Antitumor Activity by Targeting TGF-β and JAK STAT Signaling in Acute Myeloid Leukemia", 2024 [Poster 3P-126], The 47th Annual Meeting of the Molecular Biology Society of Japan (attached presentation infomation).
Gong et al., "TAS1440, an LSD1 Inhibitor, Exhibits Antitumor Activity by Targeting TGF-β and JAK STAT Signaling in Acute Myeloid Leukemia", 2024 [Poster 3P-126], The 47th Annual Meeting of the Molecular Biology Society of Japan (Abstract).
Tanaka et al., "The LSD1 inhibitor, TAS1440 suppresses neuroendocrine small cell lung cancer growth by activating TGF-β and NOTCH signaling via LSD1-INSM1 complex disruption", 2024, [Slides 3PS-14-01], The 47th Annual Meeting of the Molecular Biology Society of Japan.
Notice of Reasons for Refusal dated Jan. 14, 2025 for JP 2024-524989.
Serajuddin et al., "Salt formation to improve drug solubility", Advanced Drug Delivery Reviews, 2007, vol. 59, No. 7, pp. 603-616.
Byrn et al., "Pharmaceutical Solids: A Strategic Approach to Regulatory Considerations", 1995, vol. 12, No. 7, pp. 945-954.
Stahl, "The Practice of Medicinal Chemistry; 35 Preparation of water-soluble compounds through salt formation", The Practice of Medicinal Chemistry, 2003, pp. 601-615.
International Search Report and Written Opinion of PCT/US2022/028606, Jul. 11, 2022, 10 pages.
International Search Report and Written Opinion of PCT/US2022/047766, Feb. 24, 2023, 9 pages.
International Search Report of PCT/JP2016/085067, Jan. 31, 2017, 8 pages.
Written Opinion of PCT/JP2016/085067, Jan. 31, 2017, 9 pages.
Official Action dated Oct. 22, 2024 for RU Pat. Appln. No. 2024111538, 39 pages with English translation.
Makary et al., "Principles of salt formation", UK Journal of Pharmaceutical and Biosciences, 2014. vol. 2, No. 4, pp. 1-4.
Mashkovsky M.D. Medicines: in 2 Volumes, vol. 1.—14th ed.—Moscow: New Wave Publishing Agency, 2001.—540 p.
Ting-Chao Chou. Drug Combination Studies and Their Synergy Quantification Using the Chou-Talalay Method / Cancer Research, 2010, vol. 70, No. 2, pp. 440-446.
E. Fritz, et al., International Classification of Diseases—Oncology.—St. Petersburg: Publishing House "Questions of Oncology", 2017.—352 p.
Belousov Yu.V. et al. Clinical pharmacokinetics. Medication dosing practice.—Moscow: Litterra, 2005.—288 p.
Kharkevich D.A. Pharmacology: A textbook.—9th ed., revised, corrected and extended. Moscow: GEOTAR-Media, 2006.—736 p.
Qin et al., "Inhibition of histone lysine-specific demethylase 1 elicits breast tumor immunity and enhances antitumor efficacy of immune checkpoint blokade", Oncogene, 2019, vol. 38, No. 3, pp. 390-405.
Extended European Search Report for EP Pat Applcation No. 22876413.0, Jul. 4, 2025.

\* cited by examiner

SALT OF TERPHENYL COMPOUND

CROSS REFERENCE TO RELATED APPLICATIONS

This application is a U.S. National Stage Application under 35 U.S.C. § 371 of International Patent Application No. PCT/JP2020/042383 filed on Nov. 13, 2020, which claims the benefit under 35 U.S.C. § 119 (e) of U.S. Provisional Application No. 62/934,923 filed Nov. 13, 2019 which is incorporated herein by reference in its entirety.

TECHNICAL FIELD

The present disclosure relates to a salt of 4-[5-[(3S)-3-aminopyrrolidine-1-carbonyl]-2-[2-fluoro-4-(2-hydroxy-2-methyl-propyl) phenyl]phenyl]-2-fluoro-benzonitrile.

BACKGROUND ART

The compound 4-[5-[(3S)-3-aminopyrrolidine-1-carbonyl]-2-[2-fluoro-4-(2-hydroxy-2-methyl-propyl) phenyl]phenyl]-2-fluoro-benzonitrile (referred to herein as Compound A) has been known as a potent LSD1 inhibitor and use as an antitumor agent or an agent for preventing and/or treating cancer (PL 1).

It is desired that such an LSD1 inhibitor shows stability when it is used for a pharmaceutical formulation.

Also, there is a desire to develop such an LSD1 inhibitor that can be easily handled. It is known that the hygroscopicity of a biologically active compound affects the handling of the compound during its incorporation into a potential pharmaceutical composition. Hygroscopic compounds present problems due to their moisture absorption which leads to variations in compound mass depending on the amount of water present in the surrounding environment, making it difficult to accurately evaluate the compound's biological efficacy and to ensure the uniformity of pharmaceutical compositions containing the compound. Therefore, an active chemical compound with low hygroscopicity is desirable.

CITATION LIST

Patent Literature

PTL 1: WO2017/090756

SUMMARY OF INVENTION

Technical Problem

An object of the present application is to provide a salt of 4-[5-[(3S)-3-aminopyrrolidine-1-carbonyl]-2-[2-fluoro-4-(2-hydroxy-2-methyl-propyl) phenyl]phenyl]-2-fluoro-benzonitrile having improved stability and having no or less absorption and/or disorption property of moisture.

Solution to Problem

During a research of physicochemical properties of Compound A for the purpose of development of a formulation of Compound A, it has been found that Compound A is hygroscopic and has a characteristic of absorbing moisture in the air when a free form of Compound A is exposed to an atmosphere of high humidity and discharging moisture when exposed to an atmosphere of low humidity. In addition, analogous substances were generated after storage of Compound A.

In an industrial production of a pharmaceutical product, it is required that a drug ingredient has stability. However, the stability depends on the attribute of each compound. Therefore, it is difficult to predict a salt having appropriate properties as a drug ingredient for a pharmaceutical product. From such a point of view, the inventors have synthesized various salts of Compound A and has researched properties and stability thereof. Among these salts and a free form, the L-tartrate and the free form had the characteristic of hygroscopicity, and the succinate and the free form had a poor solid stability. It was found that only the benzoate and the sorbate were able to reduce the adsorption and/or desorption of moisture, and were stable.

For example, the present disclosure encompasses the subject matter below.

In some aspects, a benzoic acid salt of 4-[5-[(3S)-3-aminopyrrolidine-1-carbonyl]-2-[2-fluoro-4-(2-hydroxy-2-methyl-propyl) phenyl]phenyl]-2-fluoro-benzonitrile is provided.

In other aspects, a sorbic acid salt of 4-[5-[(3S)-3-aminopyrrolidine-1-carbonyl]-2-[2-fluoro-4-(2-hydroxy-2-methyl-propyl) phenyl]phenyl]-2-fluoro-benzonitrile is provided.

Advantageous Effects of Invention

The benzoic acid salt of 4-[5-[(3S)-3-aminopyrrolidine-1-carbonyl]-2-[2-fluoro-4-(2-hydroxy-2-methyl-propyl) phenyl]phenyl]-2-fluoro-benzonitrile of the present disclosure has an excellent solid stability as a drug ingredient for a pharmaceutical product, compared to Compound A in free form and the succinic acid salt, and is capable of eliminating or reducing hygroscopicity, compared to Compound A in free form and the succinic acid salt and the L-tartaric acid salt.

The sorbic acid salt of 4-[5-[(3S)-3-aminopyrrolidine-1-carbonyl]-2-[2-fluoro-4-(2-hydroxy-2-methyl-propyl) phenyl]phenyl]-2-fluoro-benzonitrile of the present disclosure also has an excellent solid stability as a drug ingredient for a pharmaceutical product, compared to Compound A in free form and the succinic acid salt, and is capable of reducing hygroscopicity, compared to Compound A in free form and the L-tartaric acid salt.

DESCRIPTION OF EMBODIMENTS

Figure 1:
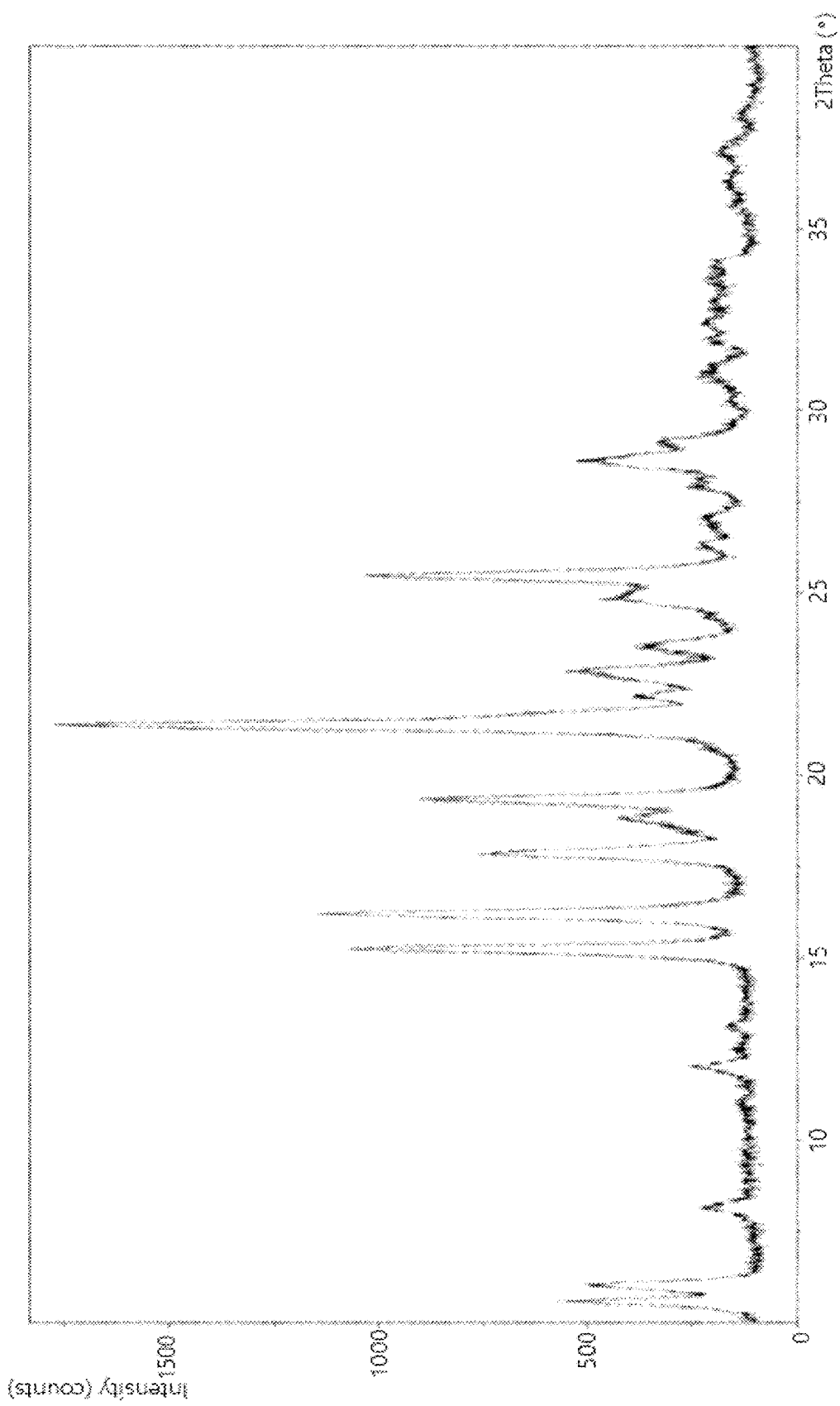
FIG. 1 is powder X-ray diffraction spectrum of a benzoic acid salt of Compound A. The axis of ordinates represents intensity (counts), and the axis of abscissas represents diffraction angle (2θ)).

In the present disclosure, "Compound A" refers to 4-[5-[(3S)-3-aminopyrrolidine-1-carbonyl]-2-[2-fluoro-4-(2-hydroxy-2-methyl-propyl) phenyl]phenyl]-2-fluoro-benzonitrile in free form. 4-[5-[(3S)-3-aminopyrrolidine-1-carbonyl]-2-[2-fluoro-4-(2-hydroxy-2-methyl-propyl) phenyl]phenyl]-2-fluoro-benzonitrile has the following structure:

[Chem.1]

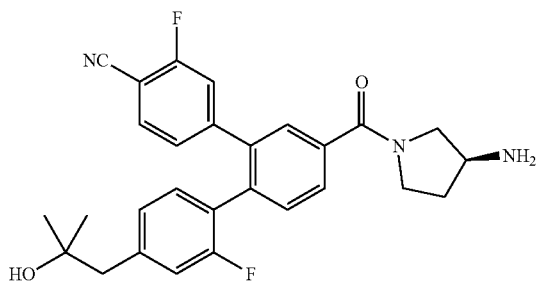

(1)

The Compound A is described as Example compound 37 of PCT Publication No. WO2017/090756, the disclosure of which is incorporated by reference herein in its entirety.

In the present disclosure, "a benzoic acid salt" and "benzoate" may be used inter-changeably.

In the present disclosure, "a sorbic acid salt" and "sorbate" may be used inter-changeably.

In a powder X-ray diffraction spectrum, a diffraction angle or a general pattern may be important in recognizing an identity of crystals, for a nature of data. Relative intensity of a powder X-ray diffraction spectrum can slightly vary depending on direction of crystal growth, size of particles, or condition of measurement, and therefore, should not be strictly interpreted.

In the present disclosure the term "diffraction angle (2θ±0.2°)" in the powder X-ray diffraction spectrum refers to a value which may be in a range within ±0.2° of a value unless otherwise indicated. A numerical value obtained from various patterns may be accompanied by a slight error due to the direction of crystal growth, size of particles, or condition of measurement thereof.

In the present disclosure, the term "in the vicinity" which is used with a peak temperature of an endothermic peak in a differential scanning calorie (DSC) curve refers to a value which approximately is the temperature, preferably refers to a value which may be within a range of ±5° C. of the value. More preferably, it refers to a value which may be in a range within ±2° C. of the value.

The salt and/or crystalline form of the present disclosure and intermediates thereof can be isolated and purified by well-known separation and purification techniques such as recrystallization, crystallization, distillation and column chromatography.

When optical isomers, stereoisomers, tautomers, or rotary isomers are possible in the salt and/or crystalline form of the present disclosure but not explicitly depicted, the salt and/or crystalline form are intended to encompass these isomers separately or as mixtures thereof. For example, unless otherwise stated, when a salt and/or crystalline form of the present disclosure appears as the racemate, the possible enantiomers and/or diastereomers that can be resolved from the racemate are also considered to be encompassed by of the present disclosure. The enantiomers and/or diastereomers can typically be obtained by well-known synthetic methods.

As used herein and unless otherwise specified, the term "crystal" and related terms used herein, when used to describe a compound, substance, modification, material, component or product, mean that the compound, substance, modification, material, component or product is substantially crystalline as determined by X-ray diffraction. See, e.g., Remington: The Science and Practice of Pharmacy, 21st edition, Lippincott, Williams and Wilkins, Baltimore, MD (2005); The United States Pharmacopeia, 23rd ed. 1843-1844 (1995).

As used herein and unless otherwise specified, the term "crystalline form" and related terms herein refer to solid forms that are crystalline. Crystalline forms include single-component crystalline forms and multiple-component crystalline forms, and may optionally include, but are not limited to, co-crystals, salts (including pharmaceutically acceptable salts), polymorphs, solvates, hydrates, and/or other molecular complexes. In certain embodiments, a crystalline form of a substance may be substantially free of amorphous forms and/or other crystalline forms. In certain embodiments, a crystalline form of a substance may contain less than about 0.1, 0.5, 1, 2, 3, 4, 5, 6, 7, 8, 9, 10, 11, 12, 13, 14, 15, 20, 25, 30, 35, 40, 45 or 50% of one or more amorphous forms and/or other crystalline forms on a weight basis.

In a certain embodiment, a crystalline form can be anhydrous. In a certain embodiment, a crystalline form can be hydrate.

As used herein and unless otherwise specified, the terms "polymorphs," "polymorphic forms" and related terms herein, refer to two or more crystalline forms that consist essentially of the same molecule, molecules, and/or ions. Like different crystalline forms, different polymorphs may have different physical properties such as, e.g., melting temperature, heat of fusion, solubility, dissolution properties and/or vibrational spectra, as a result of the arrangement or conformation of the molecules and/or ions in the crystal lattice. The differences in physical properties may affect pharmaceutical parameters such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to thermodynamically more stable polymorph) or both (e.g., tablets of one polymorph are more susceptible to breakdown at high humidity). As a result of solubility/dissolution differences, in the extreme case, some solid-state transitions may result in lack of potency or, at the other extreme, toxicity. In addition, the physical properties may be important in processing (e.g., one polymorph might be more likely to form solvates or might be difficult to filter and wash free of impurities, and particle shape and size distribution might be different between polymorphs).

As used herein and unless otherwise specified, the term "amorphous," "amorphous form," and related terms used herein, mean that the substance, component or product in question is not substantially crystalline as determined by X-ray diffraction. In particular, the term "amorphous form" describes a disordered solid form, i.e., a solid form lacking long range crystalline order.

Techniques for characterizing crystalline forms and amorphous forms include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility measurements, dissolution measurements, elemental analysis, and Karl Fischer analysis. Characteristic unit cell parameters may be determined using one or more techniques such as, but not limited to, X-ray diffraction and neutron diffraction, including single-crystal diffraction and powder diffraction. Techniques useful for analyzing powder diffraction data include profile refinement, such as Rietveld refinement, which may be used, e.g., to analyze diffraction peaks associated with a single phase in a sample comprising more than one solid phase. Other methods useful for analyzing powder diffraction data include unit cell indexing, which allows one skilled in the art to determine unit cell parameters from a sample comprising crystalline powder.

Aspects of the disclosure include a benzoic acid salt or benzoate of 4-[5-[(3S)-3-aminopyrrolidine-1-carbonyl]-2-[2-fluoro-4-(2-hydroxy-2-methyl-propyl) phenyl]phenyl]-2-fluoro-benzonitrile.

The benzoic acid salt of Compound A may be any one of salt forms of Compound A with benzoic acid, for example, monobenzoate, hemibenzoate, dibenzoate, or the like. The term is further used in a meaning involving both a crystal of benzoate of Compound A and an amorphous of benzoate of Compound A. In a preferred embodiment, the benzoate of Compound A is monobenzoate of Compound A. In another preferred embodiment, the benzoate of Compound A is a crystal. In yet another preferred embodiment, the benzoate of Compound A is a crystal of monobenzoate of Compound A.

Single crystals, including polymorphic forms, if any, and amorphous forms are included within the scope of the benzoic acid salt of the Compound A.

Such crystals can be produced by crystallization according to a crystallization method known in the art. The benzoic acid salt of the Compound A may be a solvate (e.g., a hydrate) or a non-solvate. Any of such forms are included within the scope of the salt of the present disclosure.

The benzoic acid salt of the Compound A may be a labeled form of the salt of Compound A, that is, a compound having one or more atoms of the benzoic acid salt of the Compound A substituted with a radioisotopic element or a non-radioisotopic element.

The crystal of the benzoic acid salt of Compound A may be produced through crystallization of amorphous state of the benzoic acid of Compound A, or crystallization or recrystallization of a reaction product obtained after the synthesis of benzoic acid salt of Compound A.

The benzoic acid salt of the Compound A can be produced by reacting the Compound A with benzoic acid. Compound A can be produced by any known methods in the art, including, but not limited to, those methods described in PCT Publication No. WO2017/090756, the disclosure of which is incorporated by reference herein in its entirety. The reaction of the Compound A with benzoic acid may be conducted in a solvent. Examples of solvents include, as a single solvent, hydrocarbons such as n-heptane and n-hexane; esters such as ethyl acetate, n-propyl acetate and butyl acetate; ketones such as acetone, methyl ethyl ketone, methyl isopropyl ketone and methyl isobutyl ketone; alcohols such as methanol, ethanol, 1-propanol and 2-propanol; acetonitrile; tetrahydrofuran such as tetrahydrofuran and 2-methyltetrahydrofuran and, as mixed solvents, mixed solvents of any of the above solvents and water. Examples of the preferred solvents to be used for the crystallization of the benzoic acid salt of Compound A are, but not limited to, n-heptane, ethyl acetate, methyl isobutyl ketone, methyl ethyl ketone, ethanol, a mixture of n-heptane and methyl ethyl ketone, ethanol, a mixture of ethanol and water, ketone, ethyl acetate, 2-methyltetrahydrofuran.

The amount of solvent (v/w) is preferably not less than 5 times and not more than 40 times the amount of benzoic acid salt of Compound A, more preferably not less than 5 times and not more than 20 times the amount of benzoic acid salt of Compound A, further preferably not less than 7 times and not more than 15 times the amount of benzoic acid salt of Compound A. The dissolution temperature and the crystallization temperature are preferably not less than 0° C. and not more than 100° C.

The precipitated crystals may be isolated and purified from the solution in which the crystals are dissolved, the mixed solution, or the like, by a known isolation and purification means, such as filtration, washing with an organic solvent, or drying under reduced pressure. Examples of organic solvents to be used for washing include alcohols, ketones, and acetonitrile.

In some embodiments, the crystal of the benzoic acid salt of Compound A has a powder X-ray diffraction spectrum having two or more, three or more, four or more, or five peaks of diffraction angles (2θ±0.2°) selected from the group consisting of 15.3°, 16.2°, 17.8°, 21.4° and 25.5°. The powder X-ray diffraction spectrum can be measured according to the test conditions in the EXAMPLES.

In some embodiments, the crystal of the benzoic acid salt of Compound A has a powder X-ray diffraction spectrum of FIG. 1.

In some embodiments, the crystal of the benzoic acid salt of Compound A has a peak temperature in a differential scanning calorie (DSC) curve in the range from about 188° C., 189° C., 190° C., 191° C., 192° C., 193° C. or 194° C. to about 192° C., 193° C., 194° C., 195° C., 196° C., 197° C. or 198° C. In some embodiments, the crystal of the benzoic acid salt of Compound A has a peak temperature in a DSC curve in the range from 188° C. to 198° C., from 191° C. to 195° C., from 190° C. to 194° C., or from 192° C. to 196° C. In some embodiments, the crystal of the benzoic acid salt of Compound A has a peak temperature in a DSC curve in the vicinity of 193° C.

Figure 2:
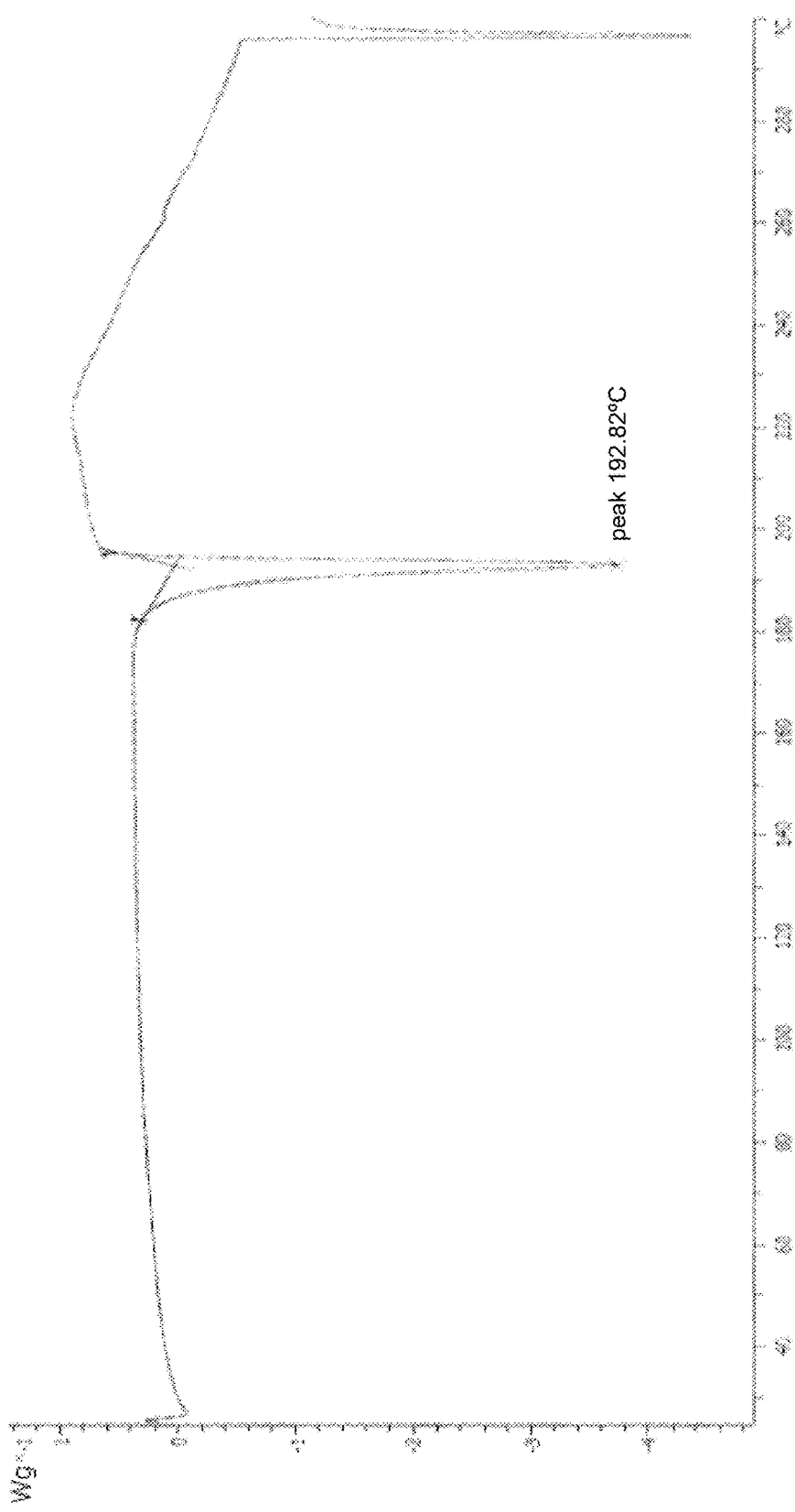
FIG. 2 is a differential scanning calorie (DSC) curve of the benzoic acid salt of Compound A. The axis of ordinates represents DSC (W/g), and the axis of abscissas represents temperature (° C.).
Figure 3:
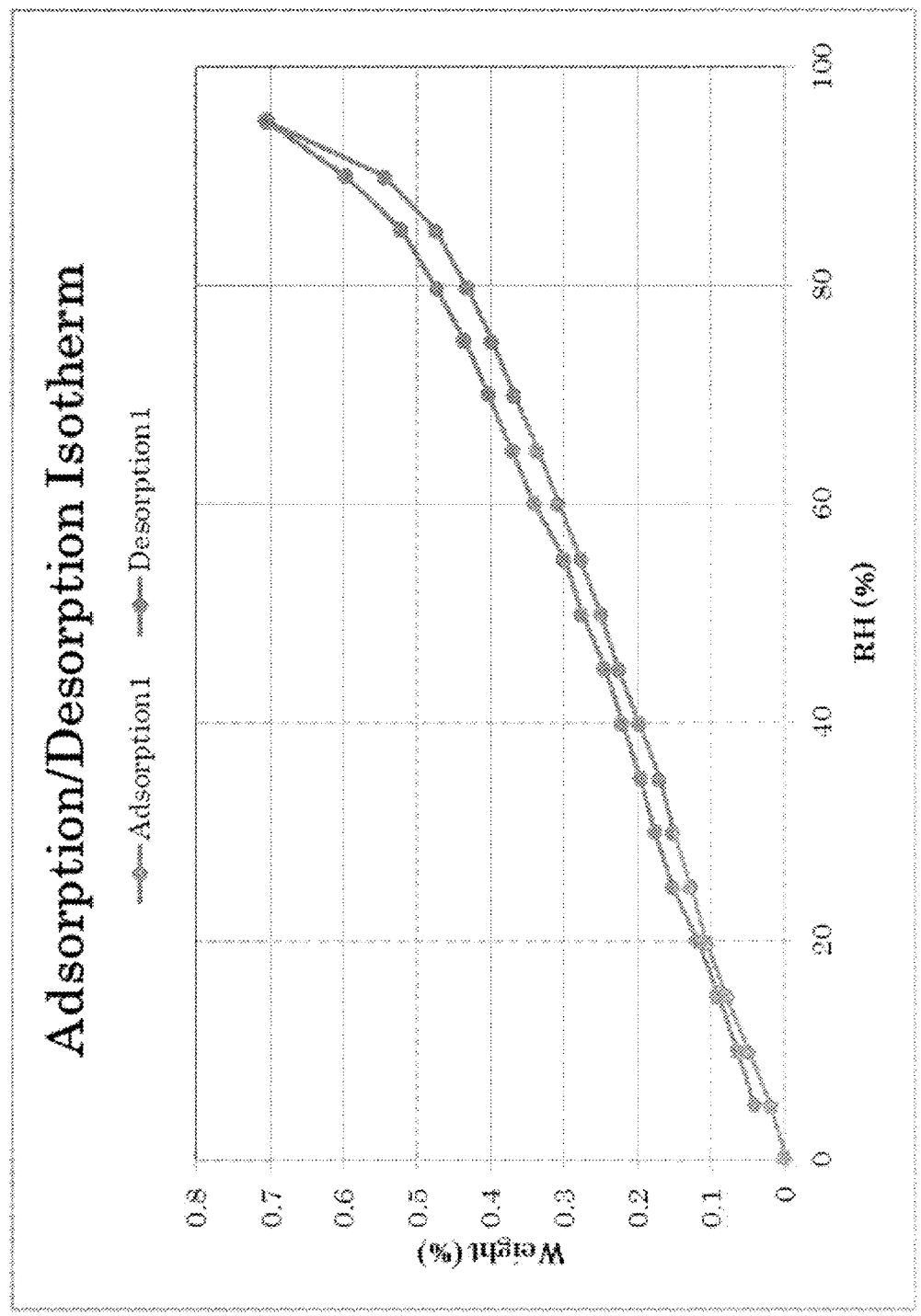
FIG. 3 is a moisture absorption/desorption isothermal curve of the benzoic acid salt of Compound A. The axis of ordinates represents weight change ratio (%), and the axis of abscissas represents relative humidity (% RH).

In some embodiments, the crystal of the benzoic acid salt of Compound A has a peak temperature of FIG. 2.

In some embodiments, the crystal of the benzoic acid salt of Compound A has a powder X-ray diffraction spectrum having two or more, three or more, four or more, or five peaks of diffraction angles (2θ±0.2°) selected from the group consisting of 15.3°, 16.2°, 17.8°, 21.4° and 25.5° and has a peak temperature in DSC curve in the range from about 188° C., 189° C., 190° C., 191° C., 192° C., 193° C. or 194° C. to about 192° C., 193° C., 194° C., 195° C., 196° C., 197° C. or 198° C.

In some embodiments, the crystal of the benzoic acid salt of Compound A has a powder X-ray diffraction spectrum having two or more, three or more, four or more, or five peaks of diffraction angles (2θ±0.2°) selected from the group consisting of 15.3°, 16.2°, 17.8°, 21.4° and 25.5° and has a peak temperature in DSC in the range from 188° C. to 198° C., from 191° C. to 195° C., from 190° C. to 194° C., or from 192° C. to 196° C., or, in the vicinity of 193° C.

In another embodiment, the crystal of the benzoic acid salt of Compound A has a powder X-ray diffraction spectrum of FIG. 1 and a peak temperature of FIG. 2 in a differential scanning calorie (DSC) curve.

In certain embodiments, the crystalline form of benzoic acid salt of Compound A disclosed herein may be physically and/or chemically pure. In certain embodiments, the crystalline form of benzoic acid salt of Compound A disclosed herein may be at least about 100, 99, 98, 97, 96, 95, 94, 93, 92, 91, 90, 89, 88, 87, 86, 85, 84, 83, 82, 81 or 80% physically and/or chemically pure. In some embodiments, the crystalline form of benzoic acid salt of Compound A disclosed herein is substantially pure. As used herein and unless otherwise specified, a sample comprising a particular crystalline form or amorphous form that is "substantially pure," e.g., substantially free of other solid forms and/or of other chemical compounds, contains, in particular embodiments, less than about 25%, 20%, 15%, 10%, 9%, 8%, 7%, 6%, 5%, 4%, 3%, 2%, 1%, 0.75%, 0.5%, 0.25% or 0.1% percent by weight of one or more other solid forms and/or of other chemical compounds.

In some embodiments, the crystalline form of benzoic acid salt of Compound A disclosed herein is stable upon exposure to conditions of about 30, 40, 50, 60, 70 or 80° C. and about 65, 70, 75, 80 or 85% relative humidity for about 1, 2, 3, 4, 5, 6, 7, 8, 12, 16, 24, 36, 48, 60, 72, 84, 96, 108, 120, 132, 144, or 156 weeks or more and for about 160, 156, 150, 138, 126, 114, 102, 90, 78, 66, 54, 42, 30, 24, 18, 12 or 6 weeks or less. The condition may be in a closed or open condition. As used herein, a "closed" condition may mean that a lid of a bottle containing the sample is closed or sealed during the stability experiment, and an "open" condition may mean that the lid is open. In additional embodiments, the crystalline form of benzoic acid salt of Compound A disclosed herein is stable upon exposure to conditions of about 40° C. and about 75% relative humidity for at least about 1, 2, 3, 4, 5, 6, 7, 8, 9, 10, 11, 12, 13, 14, 15, 16, 17, 18, 19, 20, 21, or 22 weeks. In some embodiments, the condition is a closed condition. In further embodiments, the crystalline form of benzoic acid salt of Compound A disclosed herein is stable upon exposure to conditions of about 40° C. and about 75% relative humidity for about 4 weeks. In some embodiments, the condition is a closed condition. Thus, the crystalline form of benzoic acid salt of Compound A disclosed herein exhibits excellent storage stability over an extended period. Herein, being "stable" means that (i) the change in the optical purity is about 1.0, 0.5, 0.3, 0.1, 0.05, or 0.01% or less compared to the initial optical purity, (ii) the increase in impurities is about 1.0, 0.5, 0.3, 0.1, 0.05, or 0.01% or less compared to the initial amount of impurities, and/or (iii) the X-ray diffraction pattern maintains 10, 20, 30, 40, 50, 60, 70, 80, or 90% or more of the initial peaks at (2θ±0.2°).

The benzoic acid salt of Compound A used in aspects of the disclosure are less hygroscopic than the free form of Compound A and other salts of Compound A examined. Among the free form and the salts of Compound A examined, the benzoic acid salt of Compound A is excellent in reducing the adsorption and/or disorption of moisture.

The benzoic acid salt of Compound A used in aspects of the disclosure is more excellent in solid stability than the free form of Compound A and the succinic acid salt and the sorbic acid salt of Compound A in that substantially no analogous substance is generated and the purity of the benzoic acid salt of Compound A is maintained higher than the free form of Compound A and the succinic acid salt and the sorbic acid salt after the benzoic acid salt of Compound A is stored for 4 weeks in the accerelated test. It is important for a candidate compound to be developed as a pharmaceutical product to have a solid stability, in an industrial operation and in maintaining a quality. Therefore, the benzoic acid salt of Compound A has excellent properties required for a pharmaceutical product or a drug ingredient for a pharmaceutical product.

Other aspects of the disclosure include a sorbic acid salt or sorbate of 4-[5-[(3S)-3-aminopyrrolidine-1-carbonyl]-2-[2-fluoro-4-(2-hydroxy-2-methyl-propyl) phenyl]phenyl]-2-fluoro-benzonitrile.

The sorbic acid salt of Compound A may be any one of salt forms of Compound A with sorbic acid, for example, monosorbate, hemisorbate, disorbate, or the like. The term is further used in a meaning involving both a crystal of sorbate of Compound A and an amorphous of sorbate of Compound A. In a preferred embodiment, the sorbate of Compound A is monobenzoate of Compound A. In another preferred embodiment, the sorbate of Compound A is a crystal. In yet another preferred embodiment, the sorbate of Compound A is a crystal of monosorbate of Compound A.

Single crystals, including polymorphic forms, if any, and amorphous form are included within the scope of the sorbic acid salt of Compound A.

Such crystals can be produced by crystallization according to a crystallization method known in the art. The sorbic acid salt of the Compound A may be a solvate (e.g., a hydrate) or a non-solvate. Any of such forms are included within the scope of the salt of the present disclosure.

The sorbic acid salt of the Compound A may be a labeled form of the salt of Compound A, that is, a compound having one or more atoms of the sorbic acid of the Compound A substituted with a radioisotopic element or a non-radioisotopic element.

The crystal of the sorbic acid salt of Compound A may be produced through crystallization of amorphous state of the sorbic acid salt of Compound A, or crystallization or recrystallization of a reaction product obtained after the synthesis of the sorbic acid salt of Compound A.

The sorbic acid salt of the Compound A can be produced by reacting the Compound A with sorbic acid. In preferred embodiments, the reaction of the Compound A with sorbic acid may be conducted in a solvent. Examples of solvents include, as a single solvent, hydrocarbons such as n-heptane and n-hexane; esters such as ethyl acetate, n-propyl acetate and butyl acetate; ketones such as acetone, methyl ethyl ketone, methyl isopropyl ketone and methyl isobutyl ketone; alcohols such as methanol, ethanol, 1-propanol and 2-propanol; acetonitrile; tetrahydrofuran such as tetrahydrofuran and 2-methyltetrahydrofuran and, as mixed solvents, mixed solvents of any of the above solvents and water. Examples of the preferred solvents to be used for the crystallization of the sorbic acid salt of Compound A are, but not limited to, n-heptane, and a mixture of n-heptane and alcohol such as 1-propanol and 2-propanol.

The amount of solvent (v/w) is preferably not less than 5 times and not more than 40 times the amount of sorbic acid salt of Compound A, more preferably not less than 5 times and not more than 20 times the amount of sorbic acid salt of Compound A, further preferably not less than 7 times and not more than 15 times the amount of sorbic acid salt of Compound A. The dissolution temperature and the crystallization temperature are preferably not less than 0° C. and not more than 100° C.

The precipitated crystals may be isolated and purified from the solution in which the crystals are dissolved, the mixed solution, or the like, by a known isolation and purification means, such as filtration, washing with an organic solvent, or drying under reduced pressure. Examples of organic solvents to be used for washing include alcohols, ketones, and acetonitrile.

The sorbic acid salt of Compound A used in aspects of the disclosure are less hygroscopic than the free form of Compound A and the succinic acid salt and the L-tartaric acid salt.

In some embodiments, the crystal of the sorbic acid salt of Compound A has a powder X-ray diffraction spectrum having two or more, three or more, four or more, five or more or six peaks of diffraction angles (2θ±0.2°) selected from the group consisting of 5.5°, 10.9°, 16.2°, 17.2°, 20.3° and 24.4°. The powder X-ray diffraction spectrum can be measured according to the test conditions in the EXAMPLES.

Figure 13:
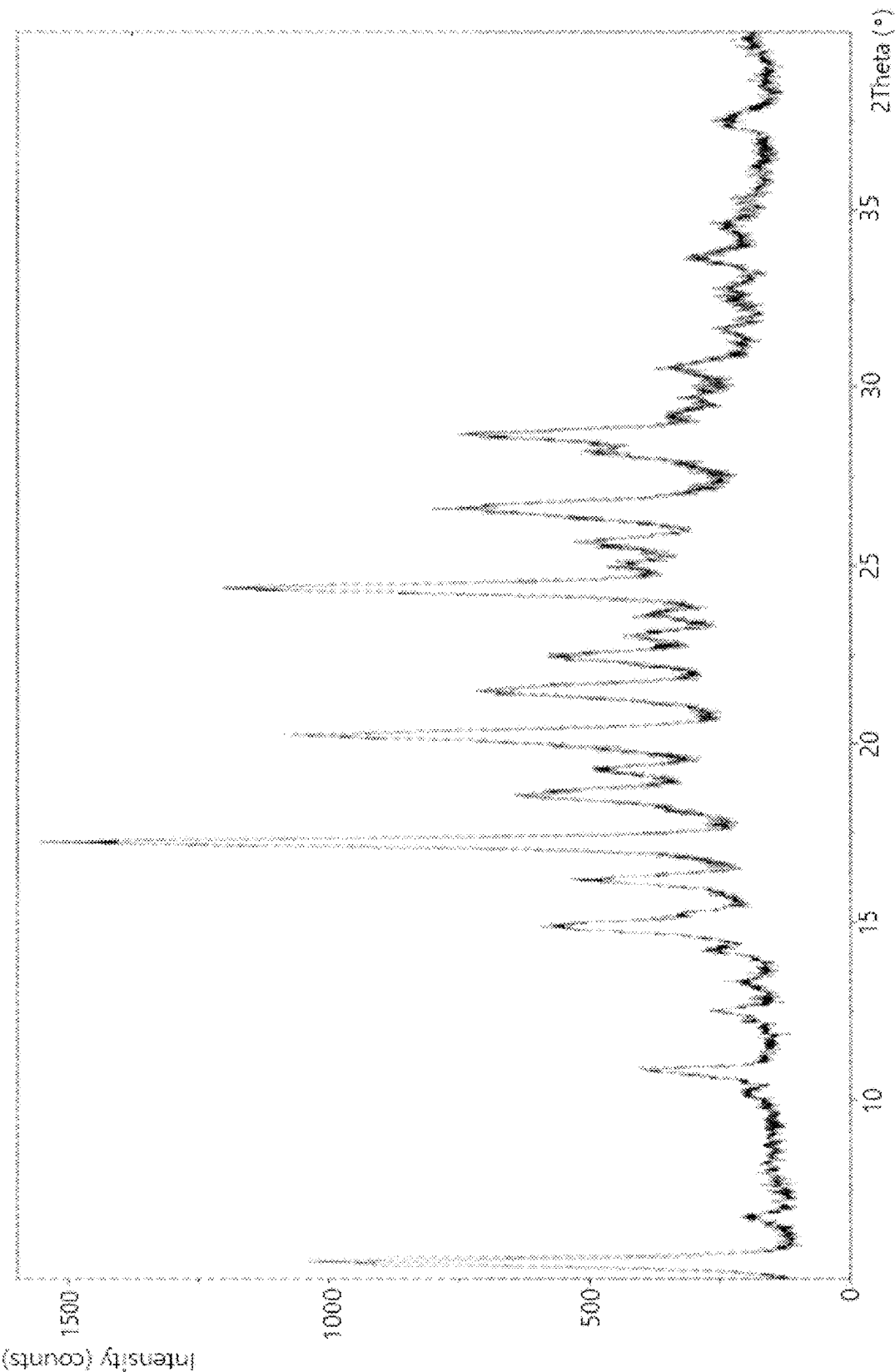
FIG. 13 is powder X-ray diffraction spectrum of a sorbic acid salt of Compound A. The axis of ordinates represents intensity (counts), and the axis of abscissas represents diffraction angle (2θ)).

In some embodiments, the crystal of the sorbic acid salt of Compound A has a powder X-ray diffraction spectrum of FIG. 13.

In some embodiments, the crystal of the sorbic acid salt of Compound A has a peak temperature in a differential scanning calorie (DSC) curve in the range from about 142° C., 143° C., 144° C., 145° C., 146° C., 147° C. or 148° C. to about 147° C., 148° C., 149° C., 150° C., 151° C., 152° C. or 153° C. In some embodiments, the crystal of the sorbic acid salt of Compound A has a peak temperature in a DSC curve in the range from 142° C. to 152° C., from 145° C. to 149° C., from 144° C. to 148° C., or from 146° C. to 149° C. In some embodiments, the crystal of the sorbic acid salt of Compound A has a peak temperature in a DSC curve in the vicinity of 147° C.

Figure 14:
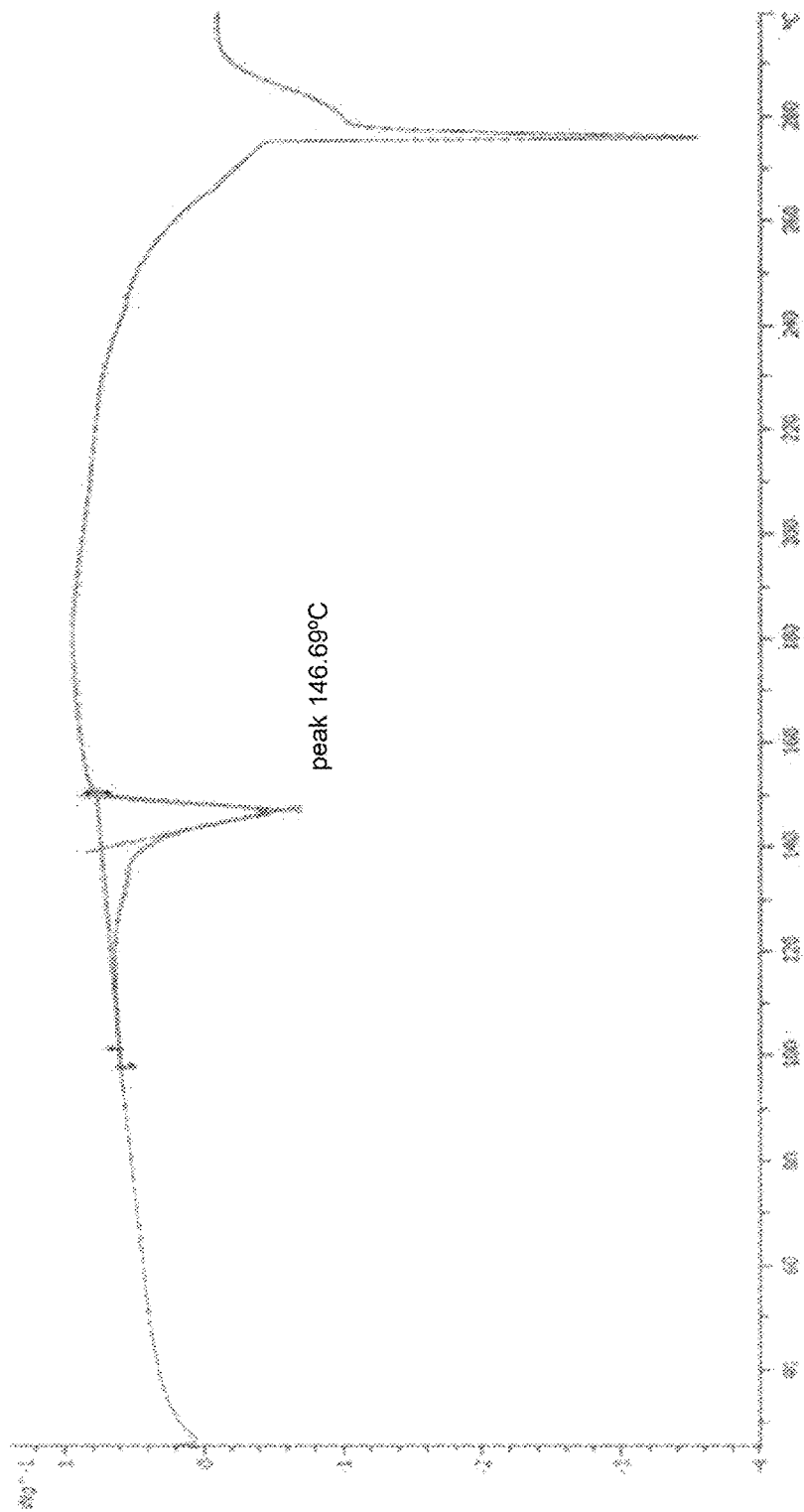
FIG. 14 is a differential scanning calorie (DSC) curve of the sorbic acid salt of Compound A. The axis of ordinates represents DSC (W/g), and the axis of abscissas represents temperature (° C.).
Figure 15:
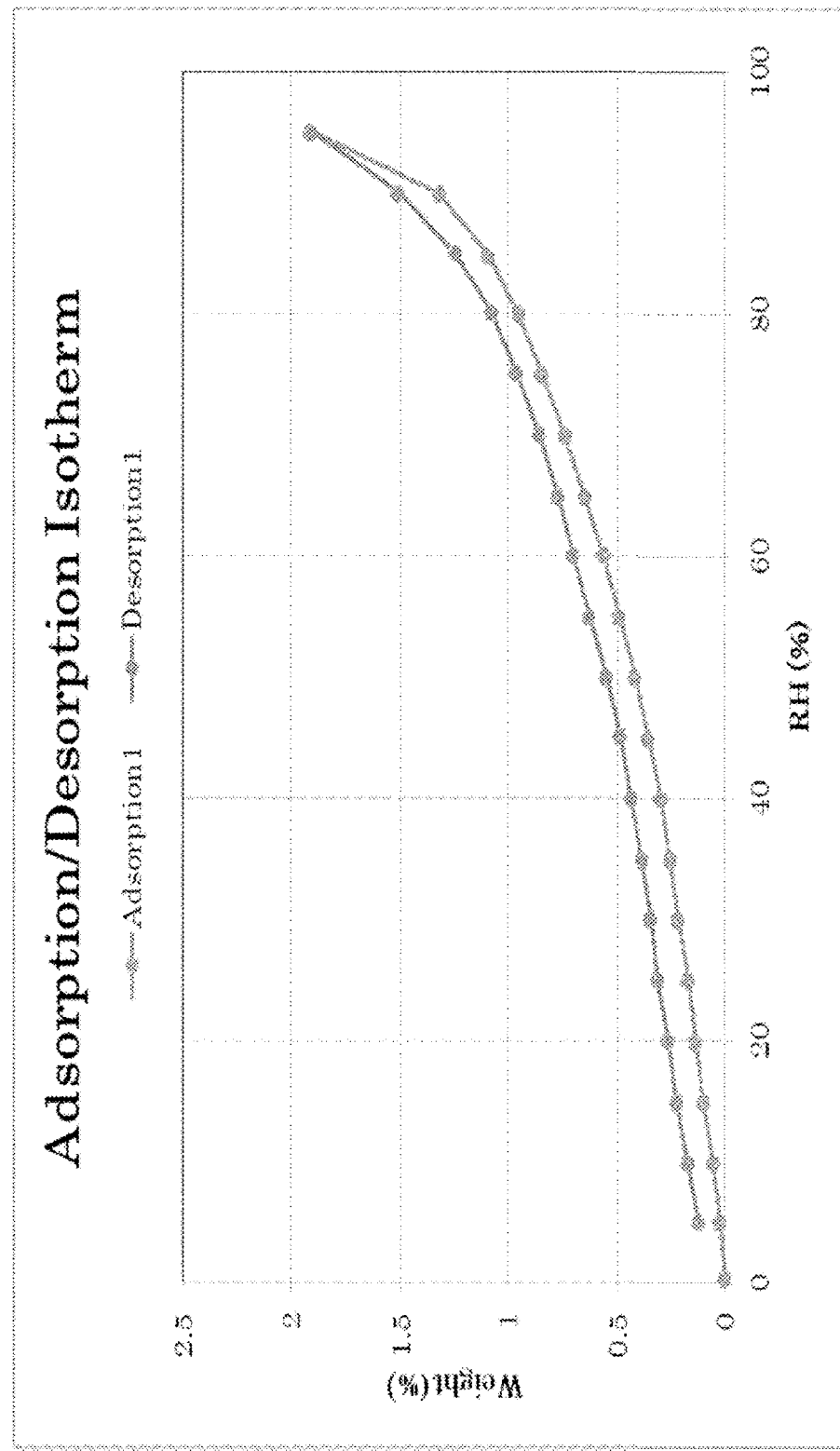
FIG. 15 is a moisture absorption/desorption isothermal curve of the sorbic acid salt of Compound A. The axis of ordinates represents weight change ratio (%), and the axis of abscissas represents relative humidity (% RH).

In some embodiments, the crystal of the sorbic acid salt of Compound A has a peak temperature of FIG. 14 in a differential scanning calorie (DSC) curve.

In some embodiments, the crystal of the sorbic acid salt of Compound A has a powder X-ray diffraction spectrum having two or more, three or more, four or more, five or more or six peaks of diffraction angles (2θ±0.2°) selected from the group consisting of 5.5°, 10.9°, 16.2°, 17.2°, 20.3° and 24.4° and has a peak temperature in a DSC curve in the range from about 1142° C., 143° C., 144° C., 145° C., 146° C., 147° C. or 148° C. to about 147° C., 148° C., 149° C., 150° C., 151° C., 152° C. or 153° C.

In some embodiments, the crystal of the sorbic acid salt of Compound A has a powder X-ray diffraction spectrum having two or more, three or more, four or more, five or more or six peaks of diffraction angles (2θ±0.2°) selected from the group consisting of 5.5°, 10.9°, 16.2°, 17.2°, 20.3° and 24.4° and has a peak temperature in a DSC curve in the range from 142° C. to 152° C., from 145° C. to 149° C., from 144° C. to 148° C., or from 146° C. to 149° C., or, in the vicinity of 147° C.

In another embodiment, the crystal of the sorbic acid salt of Compound A has a powder X-ray diffraction spectrum of FIG. 13 and a peak temperature of FIG. 14 in a differential scanning calorie (DSC) curve.

In certain embodiments, the crystalline form of sorbic acid salt of Compound A disclosed herein may be physically and/or chemically pure. In certain embodiments, the crystalline form of sorbic acid salt of Compound A disclosed herein may be at least about 100, 99, 98, 97, 96, 95, 94, 93, 92, 91, 90, 89, 88, 87, 86, 85, 84, 83, 82, 81 or 80% physically and/or chemically pure. In some embodiments, the crystalline form of sorbic acid salt of Compound A disclosed herein is substantially pure. As used herein and unless otherwise specified, a sample comprising a particular crystalline form or amorphous form that is "substantially pure," e.g., substantially free of other solid forms and/or of other chemical compounds, contains, in particular embodiments, less than about 25%, 20%, 15%, 10%, 9%, 8%, 7%, 6%, 5%, 4%, 3%, 2%, 1%, 0.75%, 0.5%, 0.25% or 0.1% percent by weight of one or more other solid forms and/or of other chemical compounds.

In some embodiments, the crystalline form of sorbic acid salt of Compound A disclosed herein is stable upon exposure to conditions of about 30, 40, 50, 60, 70 or 80° C. and about 65, 70, 75, 80 or 85% relative humidity for about 1, 2, 3, 4, 5, 6, 7, 8, 12, 16, 24, 36, 48, 60, 72, 84, 96, 108, 120, 132, 144, or 156 weeks or more and for about 160, 156, 150, 138, 126, 114, 102, 90, 78, 66, 54, 42, 30, 24, 18, 12 or 6 weeks or less. The condition may be in a closed or open condition. As used herein, a "closed" condition may mean that a lid of a bottle containing the sample is closed or sealed during the stability experiment, and an "open" condition may mean that the lid is open. In additional embodiments, the crystalline form of sorbic acid salt of Compound A disclosed herein is stable upon exposure to conditions of about 40° C. and about 75% relative humidity for at least about 1, 2, 3, 4, 5, 6, 7, 8, 9, 10, 11, 12, 13, 14, 15, 16, 17, 18, 19, 20, 21, or 22 weeks. In some embodiments, the condition is a closed condition. In further embodiments, the crystalline form of sorbic acid salt of Compound A disclosed herein is stable upon exposure to conditions of about 40° C. and about 75% relative humidity for about 4 weeks. In some embodiments, the condition is a closed condition. Thus, the crystalline form of sorbic acid salt of Compound A disclosed herein exhibits excellent storage stability over an extended period. Herein, being "stable" means that (i) the change in the optical purity is about 1.0, 0.5, 0.3, 0.1, 0.05, or 0.01% or less compared to the initial optical purity, (ii) the increase in impurities is about 1.0, 0.5, 0.3, 0.1, 0.05, or 0.01% or less compared to the initial amount of impurities, and/or (iii) the X-ray diffraction pattern maintains 10, 20, 30, 40, 50, 60, 70, 80, or 90% or more of the initial peaks at (2θ±0.2°).

The sorbic acid salt of Compound A used in aspects of the disclosure is more excellent in solid stability than the free form of Compound A and the succinic acid salt of Compound A in that only a small amount of analogous substance is generated and the purity of the sorbic acid salt of Compound A is maintained higher than the free form of Compound A and the succinic acid salt after the sorbic acid salt of Compound A is stored for 4 weeks in the accelerated test. It is important for a candidate compound to be developed as a pharmaceutical product to have a solid stability, in an industrial operation and in maintaining a quality. Therefore, the sorbic acid salt of Compound A has excellent properties required for a pharmaceutical product or a drug ingredient for a pharmaceutical product.

The benzoic acid salt of Compound A and the sorbic acid salt of Compound A have excellent solid stability and low hygroscopicity. Thus, these salts are useful as a raw material of a pharmaceutical composition.

The benzoic acid salt of Compound A and the sorbic acid salt of Compound A have excellent LSD1 inhibitory activity so that these compounds are useful as a pharmaceutical preparation for preventing and treating LSD1-related diseases.

The term "LSD1-related diseases or disorders" include diseases, the incidence of which can be reduced, and symptoms of which can be remitted, relieved, and/or completely cured by eliminating, suppressing, and/or inhibiting LSD1 function. Examples of such diseases include, but are not limited to, malignant tumors, etc. The type of malignant tumor to be treated by the Compound A or a salt thereof is not particularly limited. Examples of such malignant tumors include head and neck cancers, esophagus cancer, gastric cancer, colon cancer, rectum cancer, liver cancer, gallbladder cancer, cholangiocarcinoma, biliary tract cancer, pancreatic cancer, lung cancer, breast cancer, ovarian cancer, cervical cancer, endometrial cancer, renal cancer, bladder cancer, prostate cancer, testicular tumor, osteosarcoma, soft-tissue sarcoma, leukemia, myelodysplastic syndrome, chronic myeloproliferative disease, malignant lymphoma, multiple myeloma, skin cancer, brain tumor, mesothelioma, and the like. Preferable examples include lung cancers (e.g., non-small cell lung cancer and small cell lung cancer), leukemia, and myelodysplastic syndromes. More preferably, examples include lung cancers (non-small-cell lung cancer, small-cell lung cancer, etc.) and leukemia.

Each of the benzoic acid salt of Compound A and the sorbic acid salt of Compound A may be processed, after being pulverized or without being pulverized, into various forms of pharmaceutical composition, for example tablets, capsules, granules, fine granules, powdered drug, dry syrup and like oral preparations, suppositories, inhalation agents, nasal drops, ointments, patches, aerosols and like external preparations, and injections. Of these, oral preparations are preferable.

When the benzoic acid salt of Compound A or the sorbic acid salt of Compound A is used as a pharmaceutical preparation a pharmaceutical carrier can be added, if required, thereby forming a suitable dosage form according to prevention and treatment purposes. Examples of the dosage form include oral preparations, injections, suppositories, ointments, patches, and the like. Of these, oral preparations are preferable. Such dosage forms can be formed by methods conventionally known to persons skilled in the art.

As the pharmaceutical carrier, various conventional organic or inorganic carrier materials used as preparation materials may be used. For example, such materials can be blended as an excipient, binder, disintegrant, lubricant, or coating agent in solid preparations; or as a solvent, solubilizing agent, suspending agent, isotonizing agent, pH adjuster, buffer, or soothing agent in liquid preparations. Moreover, pharmaceutical preparation additives, such as antiseptics, antioxidants, colorants, taste-masking or flavoring agents, and stabilizers, can also be used, if required.

Oral solid preparations are prepared as follows. After an excipient is added optionally with a binder, disintegrant, lubricant, colorant, taste-masking or flavoring agent, etc., to the benzoic acid salt of Compound A or the sorbic acid salt of Compound A, the resulting mixture is formulated into tablets, coated tablets, granules, powders, capsules, or the like by methods known in the art.

Examples of excipients include lactose, sucrose, D-mannitol, glucose, starch, calcium carbonate, kaolin, microcrystalline cellulose, and silicic acid anhydride. Examples of binders include water, ethanol, 1-propanol, 2-propanol, simple syrup, liquid glucose, liquid α-starch, liquid gelatin, D-mannitol, carboxymethyl cellulose, hydroxypropyl cellulose, hydroxypropyl starch, methyl cellulose, ethyl cellulose, shellac, calcium phosphate, polyvinylpyrrolidone, and the like. Examples of disintegrators include dry starch, sodium alginate, powdered agar, sodium hydrogen carbonate, calcium carbonate, sodium lauryl sulfate, stearic acid monoglyceride, lactose, and the like. Examples of lubricants include purified talc, stearic acid salt sodium, magnesium stearate, borax, polyethylene glycol, and the like. Examples of colorants include titanium oxide, iron oxide, and the like. Examples of taste-masking or flavoring agents include sucrose, bitter orange peel, citric acid, L-tartaric acid, and the like.

When a liquid preparation for oral administration is prepared, a taste-masking agent, a buffer, a stabilizer, a flavoring agent, and the like may be added to the benzoic acid salt of Compound A or the sorbic acid salt of Compound A and the resulting mixture may be formulated into an oral liquid preparation, syrup, elixir, etc., according to an ordinary method.

In this case, the same taste-masking or flavoring agent as those mentioned above may be used. Examples of the buffer include sodium citrate and the like, and examples of the stabilizer include tragacanth, gum arabic, gelatin, and the like. As necessary, these preparations for oral administration may be coated according to methods known in the art with an enteric coating or other coating for the purpose of, for example, persistence of effects. Examples of such coating agents include hydroxypropyl methylcellulose, ethyl cellulose, hydroxymethyl cellulose, hydroxypropyl cellulose, polyoxyethylene glycol, and Tween 80 (registered trademark).

When an injection is prepared, a pH adjuster, a buffer, a stabilizer, an isotonizing agent, a topical anesthetic, and the like may be added, as necessary, to the the benzoic acid salt of Compound A and the sorbic acid salt of Compound A; and the resulting mixture may be formulated into subcutaneous, intramuscular, and intravenous injections according to an ordinary method.

Examples of usable pH adjusters and buffers include sodium citrate, sodium acetate, sodium phosphate, and the like. Examples of usable stabilizers include sodium pyrosulfite, EDTA, thioglycolic acid, and thiolactic acid. Examples of usable topical anesthetics include procaine hydrochloride, lidocaine hydrochloride, and the like. Examples of usable isotonizing agents include sodium chloride, glucose, D-mannitol, glycerin, and the like.

The amount of each of the benzoic acid salt of Compound A and the sorbic acid salt of Compound A to be incorporated in each of such dosage unit forms depends on the condition of the patient to whom the compound is administered, the dosage form, etc. In general, in the case of an oral agent, an injection, and a suppository, the amount of the compound of the present disclosure is preferably 0.05 to 1000 mg, 0.01 to 500 mg, and 1 to 1000 mg, respectively, per dosage unit form.

The daily dose of the medicine in such a dosage form depends on the condition, body weight, age, gender, etc., of the patient, and cannot be generalized. For example, the daily dose of the benzoic acid salt of Compound A or the sorbic acid salt of Compound A for an adult (body weight: 50 kg) may be usually 0.05 to 5000 mg, and preferably 0.1 to 1000 mg; and is preferably administered in one dose, or in two to three divided doses, per day.

Notwithstanding the appended claims, aspects of the present disclosure and exemplary embodiments are described by the following clauses:

Clause [1]
A benzoic acid salt of 4-[5-[(3S)-3-aminopyrrolidine-1-carbonyl]-2-[2-fluoro-4-(2-hydroxy-2-methyl-propyl) phenyl]phenyl]-2-fluoro-benzonitrile.

Clause [2]
The benzoic acid salt according to Clause 1 wherein the salt comprises a crystal.

Clause [3]
The benzoic acid salt according to Clause 2 wherein the crystal is an anhydrous.

Clause [4]
The benzoic acid salt according to Clause 2 wherein the crystal is a hydrate.

Clause [5]
The benzoic acid salt according to Clause 2 wherein the crystal has a powder X-ray diffraction spectrum having at least two peaks of diffraction angles (2θ±0.2°) selected from the group consisting of 15.3°, 16.2°, 17.8°, 21.4° and 25.5°.

Clause [6]
The benzoic acid salt according to Clause 2 wherein the crystal has a powder X-ray diffraction spectrum having peaks of diffraction angles (2θ±0.2°) of 15.3°, 16.2°, 17.80, 21.40 and 25.50.

Clause [7]
The benzoic acid salt according to any one of Clauses 2 to 6 wherein the crystal has a peak temperature in a differential scanning calorie (DSC) curve with an endothermic peak in the vicinity of 193° C.

Clause [8]
The benzoic acid salt according to any one of Clauses 2 to 6 wherein the crystal has a peak temperature in a differential scanning calorie (DSC) curve with an endothermic peak in the range from 188° C. to 198° C.

Clause [9]
The benzoic acid salt according to any one of Clauses 2 to 8 wherein the optical purity of the crystalline form of the benzoic acid salt of Compound A is at least about 70, 80, 85, 90, 91, 92, 93, 94, 95, 96, 97, 98, 99, 99.5 or 99.8%.

Clause [10]
The benzoic acid salt according to any one of Clauses 2 to 9 wherein the crystal has a powder X-ray diffraction spectrum of FIG. 1.

Clause [11]
A sorbic acid salt of 4-[5-[(3S)-3-aminopyrrolidine-1-carbonyl]-2-[2-fluoro-4-(2-hydroxy-2-methyl-propyl) phenyl]phenyl]-2-fluoro-benzonitrile.

Clause [12]
The sorbic acid salt according to Clause 11 wherein the salt comprises a crystal.

Clause [13]
The sorbic acid salt according to Clause 12 wherein the crystal is an anhydrous.

Clause [14]
The sorbic acid salt according to Clause 12 wherein the crystal is a hydrate.

Clause [15]
The sorbic acid salt according to Clause 12 wherein the crystal has a powder X-ray diffraction spectrum having at least two peaks of diffraction angles (2θ±0.2°) selected from the group consisting of 5.5°, 10.9°, 16.2°, 17.2°, 20.3° and 24.4°.

Clause [16]
The sorbic acid salt according to Clause 12 wherein the crystal has a powder X-ray diffraction spectrum having peaks of diffraction angles (2θ±0.2°) of 15.3°, 16.2°, 17.80, 21.40 and 25.50.

Clause [17]
The sorbic acid salt according to any one of Clauses 12 to 16 wherein the crystal has a peak temperature in a differential scanning calorie (DSC) curve with an endothermic peak in the vicinity of 147° C.

Clause [18]
The sorbic acid salt according to any one of Clauses 12 to 16 wherein the crystal has a peak temperature in a differential scanning calorie (DSC) curve with an endothermic peak in the range from 142° C. to 152° C.

Clause [19]
The sorbic acid salt according to any one of Clauses 12 to 18 wherein the optical purity of the crystalline form of the sorbic acid salt of Compound A is at least about 70, 80, 85, 90, 91, 92, 93, 94, 95, 96, 97, 98, 99, 99.5 or 99.8%.

Clause [20]
The sorbic acid salt according to any one of Clauses 12 to 19 wherein the crystal fumarate has a powder X-ray diffraction spectrum of FIG. 13.

Clause [21]
An LSD1 inhibitor comprising the salt according to any one of Clauses 1 to 20, as an active ingredient.

Clause [22]
A pharmaceutical composition comprising the salt according to any one of Clauses 1 to 20.

Clause [23]
The pharmaceutical composition according to Clause 22 wherein the composition is a pharmaceutical composition for preventing or treating an LSD1-related disease or disorder.

Clause [24]
The pharmaceutical composition according to Clause 22 or 23 which is an orally administered composition.

Clause [25]
An antitumor agent comprising the salt according to any one of Clauses 1 to 20, as an active ingredient.

Clause [26]
A method of treating an LSD1-related disease or disorder in a patient in need, the method comprising administering an effective amount of any one of Clauses 1 to 20 to the patient.

Clause [27]
The salt compound according to any one of Clauses 1 to 20 for use in preventing and/or treating an LSD1-related disease or disorder.

Clause [28]
Use of the salt according to any one of Clauses 1 to 20 in the manufacture of an antitumor agent.

Clause [29]

A production method of a benzoic acid salt of 4-[5-[(3S)-3-aminopyrrolidine-1-carbonyl]-2-[2-fluoro-4-(hydroxy-2-methyl-propyl) phenyl]phenyl]-2-fluoro-benzonitrile, the method comprising:

reacting 4-[5-[(3S)-3-aminopyrrolidine-1-carbonyl]-2-[2-fluoro-4-(2-hydroxy-2-methyl-propyl) phenyl]phenyl]-2-fluoro-benzonitrile with a benzoic acid.

Clause [30]

A production method of a crystal of benzoic acid salt of 4-[5-[(3S)-3-aminopyrrolidine-1-carbonyl]-2-[2-fluoro-4-(2-hydroxy-2-methyl-propyl) phenyl]phenyl]-2-fluoro-benzonitrile, the method comprising:

mixing 4-[5-[(3S)-3-aminopyrrolidine-1-carbonyl]-2-[2-fluoro-4-(2-hydroxy-2-methyl-propyl) phenyl]phenyl]-2-fluoro-benzonitrile with a benzoic acid in a solvent, and isolating the resultant benzoic acid salt of 4-[5-[(3S)-3-aminopyrrolidine-1-carbonyl]-2-[2-fluoro-4-(2-hydroxy-2-methyl-propyl) phenyl]phenyl]-2-fluoro-benzonitrile in a crystalline form.

Clause [31]

The production method according to Clause 30, wherein the solvent comprises hydrocarbon, an ester, ketone, alcohol, acetonitrile, tetrahydrofurane, a mixture of any of the said solvents, or a mixture of one or more of the said solvents and water.

Clause [32]

A production method of a sorbic acid salt of 4-[5-[(3S)-3-aminopyrrolidine-1-carbonyl]-2-[2-fluoro-4-(2-hydroxy-2-methyl-propyl) phenyl]phenyl]-2-fluoro-benzonitrile, the method comprising:

reacting 4-[5-[(3S)-3-aminopyrrolidine-1-carbonyl]-2-[2-fluoro-4-(2-hydroxy-2-methyl-propyl) phenyl]phenyl]-2-fluoro-benzonitrile with a sorbic acid.

Clause [33]

A production method of a crystal of sorbic acid salt of 4-[5-[(3S)-3-aminopyrrolidine-1-carbonyl]-2-[2-fluoro-4-(2-hydroxy-2-methyl-propyl) phenyl]phenyl]-2-fluoro-benzonitrile, the method comprising:

mixing 4-[5-[(3S)-3-aminopyrrolidine-1-carbonyl]-2-[2-fluoro-4-(2-hydroxy-2-methyl-propyl) phenyl]phenyl]-2-fluoro-benzonitrile with sorbic acid in a solvent, and isolating the resultant sorbic acid salt of 4-[5-[(3S)-3-aminopyrrolidine-1-carbonyl]-2-[2-fluoro-4-(2-hydroxy-2-methyl-propyl) phenyl]phenyl]-2-fluoro-benzonitrile in a crystalline form.

Clause [34]

The production method according to Clause 33, wherein the solvent comprises hydrocarbon, an ester, ketone, alcohol, acetonitrile, tetrahydrofurane, a mixture of any of the said solvents, or a mixture of one or more of the said solvents and water.

EXAMPLES

The disclosure will now be illustrated, but not limited, by reference to the specific embodiments described in the following examples.

1. Powder X-Ray Diffraction Measurement

The powder X-ray diffraction was measured in accordance with the following test conditions, after a test substance is lightly pulverized as needed in an agate mortar.

Device: EMPYREAN, Malvern PANalytical
Reflection method (focusing method)
Target: Cu
X-ray tube current: 40 mA
X-ray tube voltage: 45 kV
Scanning area: 2θ=5.0 to 40.0°
Step size: 2θ=0.01310
Scanning speed: 0.0015/sec.
Divergence Slit: 1°
Scattering Slit: 2.0 mm
Light receiving slit: 8.0 mm Handling of the devices including data processing was based on the method and the process indicated in each device.

Numerical values obtained from various spectrums may slightly fluctuate according to direction of crystal growth, size of particles, or condition of measurement thereof. Therefore, those numerical values should not be strictly interpreted.

2. Differential Scanning Calorie Measurement (DSC Measurement)

DSC measurement was measured in accordance with the following test conditions.

Device: DSC1 STAR System, SETTLER TOLEDO
Sample: About 1 mg (except for 0.5 mg for the L-tartaric acid salt)
Sample container: Aluminum made
Temperature rising scope: from 25° C. to 300° C.
Temperature rising speed: 10° C./min.
Atmospheric gas: Nitrogen
Flow rate of nitrogen gas: 30 mL/min.

Handling of the devices including data processing was based on the method and the process indicated in each device.

Production Example 1: Preparation of 4-[5-[(3S)-3-aminopyrrolidine-1-carbonyl]-2-[2-fluoro-4-(2-hydroxy-2-methyl-propyl) phenyl]phenyl]-2-fluoro-benzonitrile (Compound A)

The Compound A was prepared by the method for the synthetization of Example compound 37 described in PCT Publication No. WO2017/090756.

Production Example 2: Synthesis of a Crystal of a Benzoic Acid Salt of Compound A 260 mg of benzoic acid was dissolved in 26 mL of methyl isobutyl ketone and the mixture was added to 1000 mg of the Compound A obtained according to the method of Production Example 1. The suspension was stirred for approximately 16.5 hours at room temperature, filtered, and the solid was collected and dried to yield 845.2 mg of the titled crystal (yield: 67%).

Powder X-ray diffraction, differential scanning calorie (DSC) measurement and moisture absorption/desorption test were carried out with respect to the obtained crystal.

FIG. 1 is powder X-ray diffraction spectrum of the crystal of the benzoic acid salt of Compound A. FIG. 2 is a differential scanning calorie (DSC) curve of the crystal of the benzoic acid salt of Compound A.

In FIG. 1, the crystal of the benzoic acid salt of Compound A had characteristic peaks at diffraction angles (2θ±0.2°) of 15.3°, 16.2°, 17.8°, 21.4° and 25.5° in the powder X-ray diffraction spectrum. The molar ratio of the compound A to benzoic acid in the product was 1:1.

In FIG. 2, the crystal has a peak temperature in a differential scanning calorie (DSC) curve with an endothermic peak in the vicinity of 193° C.

Production Example 3: Synthesis of a Crystal of a
Free Form (Free Base) of Compound A 4 mL of diisopropyl ether was added to 400 mg of the Compound A obtained according to the method of Production Example 1. The suspension was stirred overnight at 50° C., filtered, and the solid was collected and dried to yield 310 mg of the titled crystal (yield: 78%).

Figure 4:
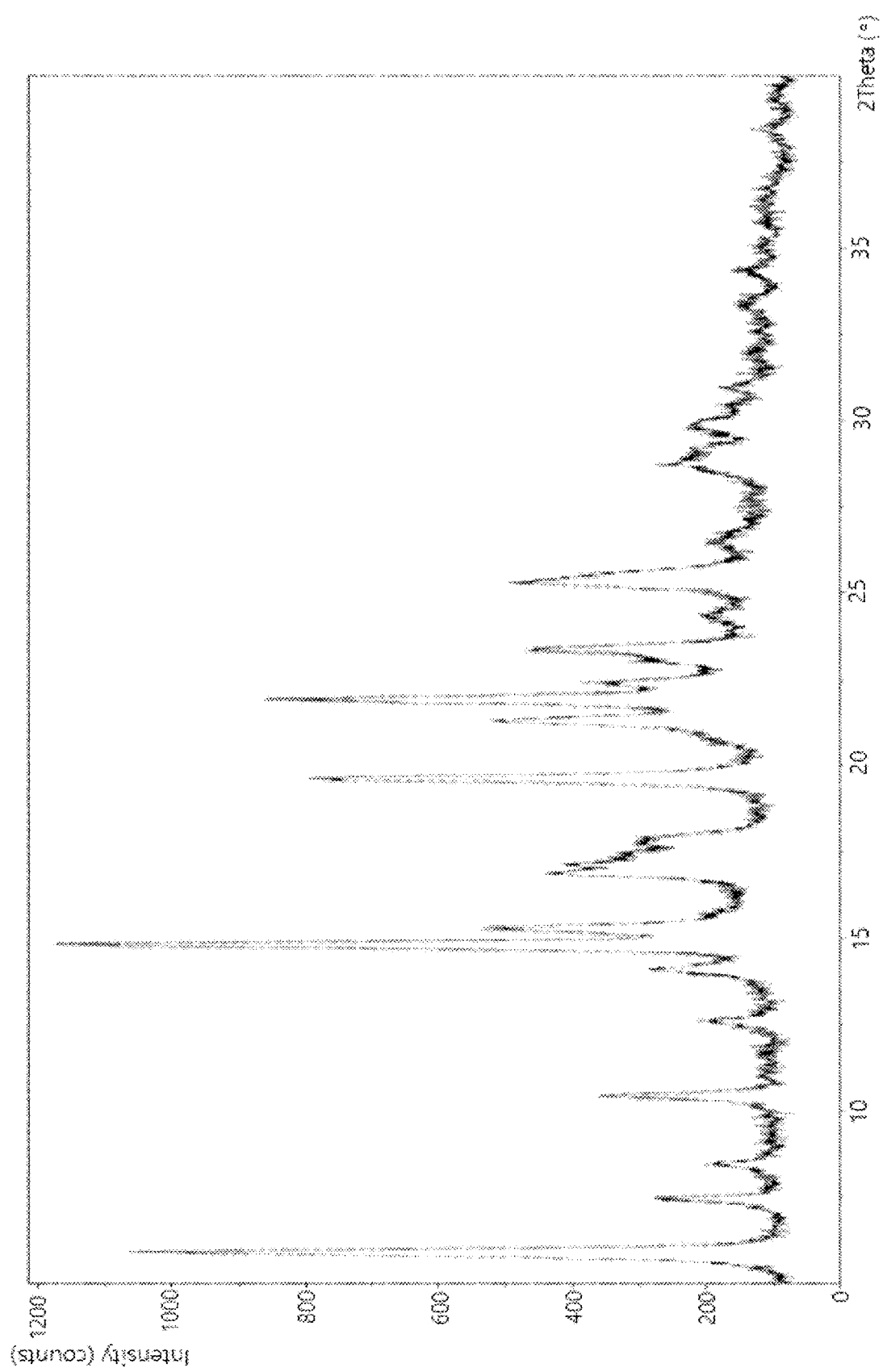
FIG. 4 is powder X-ray diffraction spectrum of a free form Form C of Compound A. The axis of ordinates represents intensity (counts), and the axis of abscissas represents diffraction angle (2θ)).
Figure 5:
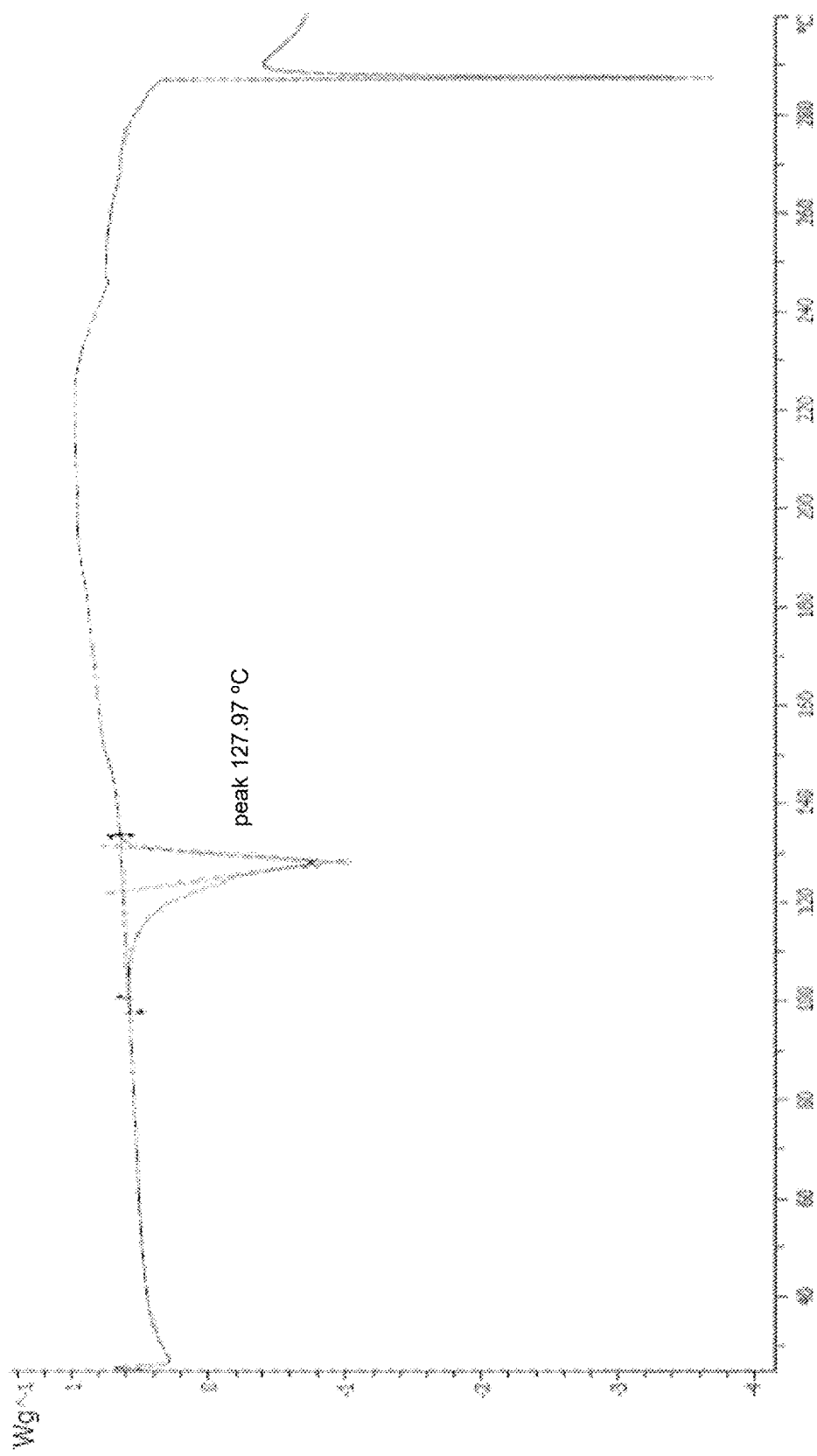
FIG. 5 is a differential scanning calorie (DSC) curve of the free form Form C of Compound A. The axis of ordinates represents DSC (W/g), and the axis of abscissas represents temperature (° C.).

Powder X-ray diffraction, differential scanning calorie (DSC) measurement and moisture absorption/desorption test were carried out with respect to the obtained crystal FIG. 4 is powder X-ray diffraction spectrum of the crystal of the free form Form C of Compound A. The crystal of the free form Form C is the most thermodynamically stable crystal form among the crystals of the free form of Compound A. FIG. 5 is a differential scanning calorie (DSC) curve of the crystal of the free form Form C of Compound A.

In FIG. 4, the crystal of the free form of Compound A had characteristic peaks at diffraction angles (2θ±0.2°) of 5.9°, 7.5°, 10.4°, 14.8°, 19.7° and 22.0° in the powder X-ray diffraction spectrum.

In FIG. 5, the crystal has a peak temperature in a differential scanning calorie (DSC) curve with an endothermic peak in the vicinity of 138° C.

Production Example 4: Synthesis of a Crystal of a
Succinic Acid Salt of Compound A 240 mg of succinic acid and 15 mL of acetonitrile were added to 600 mg of the crystal of free form Form C (i.e., free base) of Compound A obtained according to the method of Production Example 3. The suspension was stirred about two hours at 50° C., filtered, and the solid was collected and dried to yield 634 mg of the titled crystal (yield: 85%).

Figure 7:
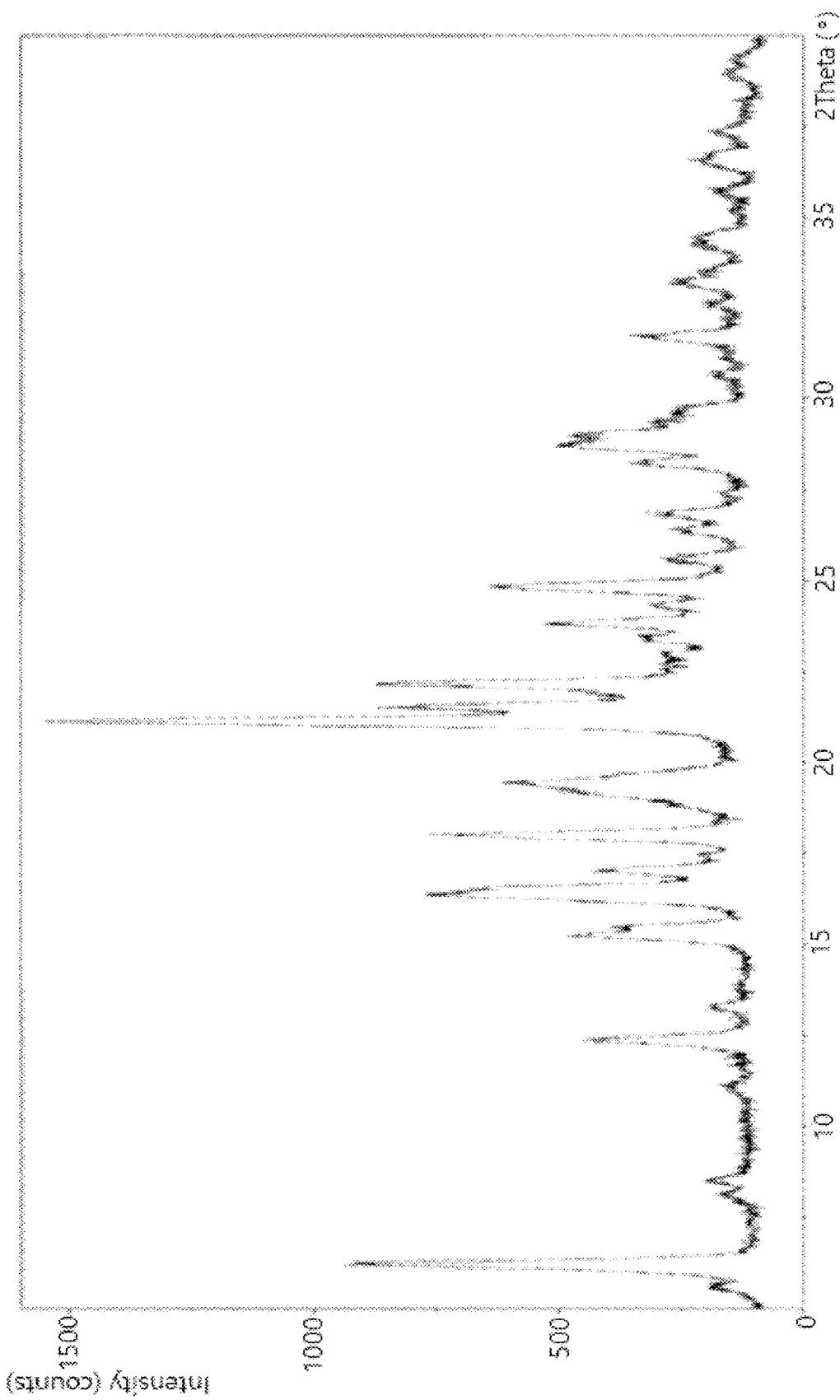
FIG. 7 is powder X-ray diffraction spectrum of a succinic acid salt of Compound A. The axis of ordinates represents intensity (counts), and the axis of abscissas represents diffraction angle (2θ)).
Figure 8:
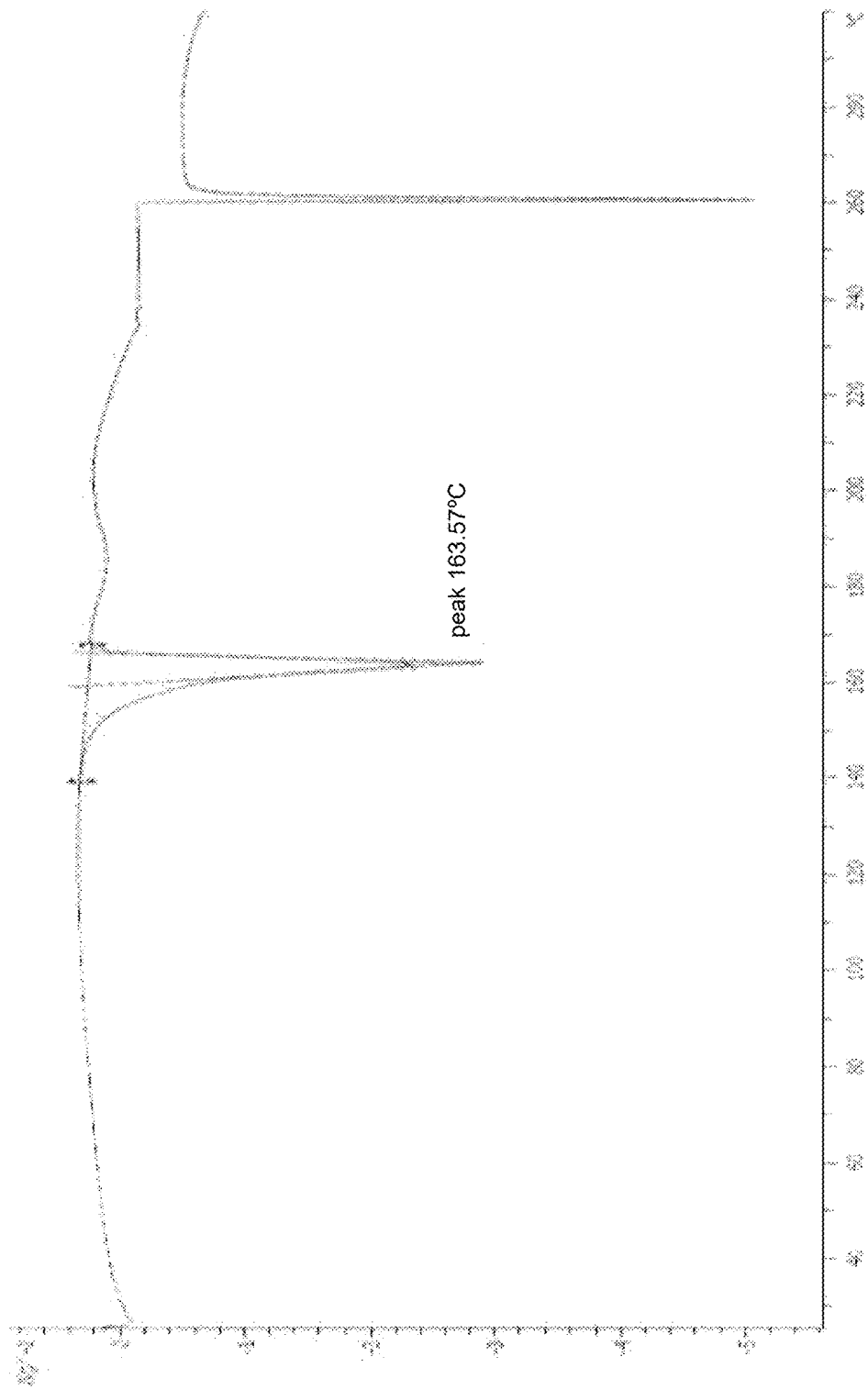
FIG. 8 is a differential scanning calorie (DSC) curve of the succinic acid salt of Compound A. The axis of ordinates represents DSC (W/g), and the axis of abscissas represents temperature (° C.).
Figure 9:
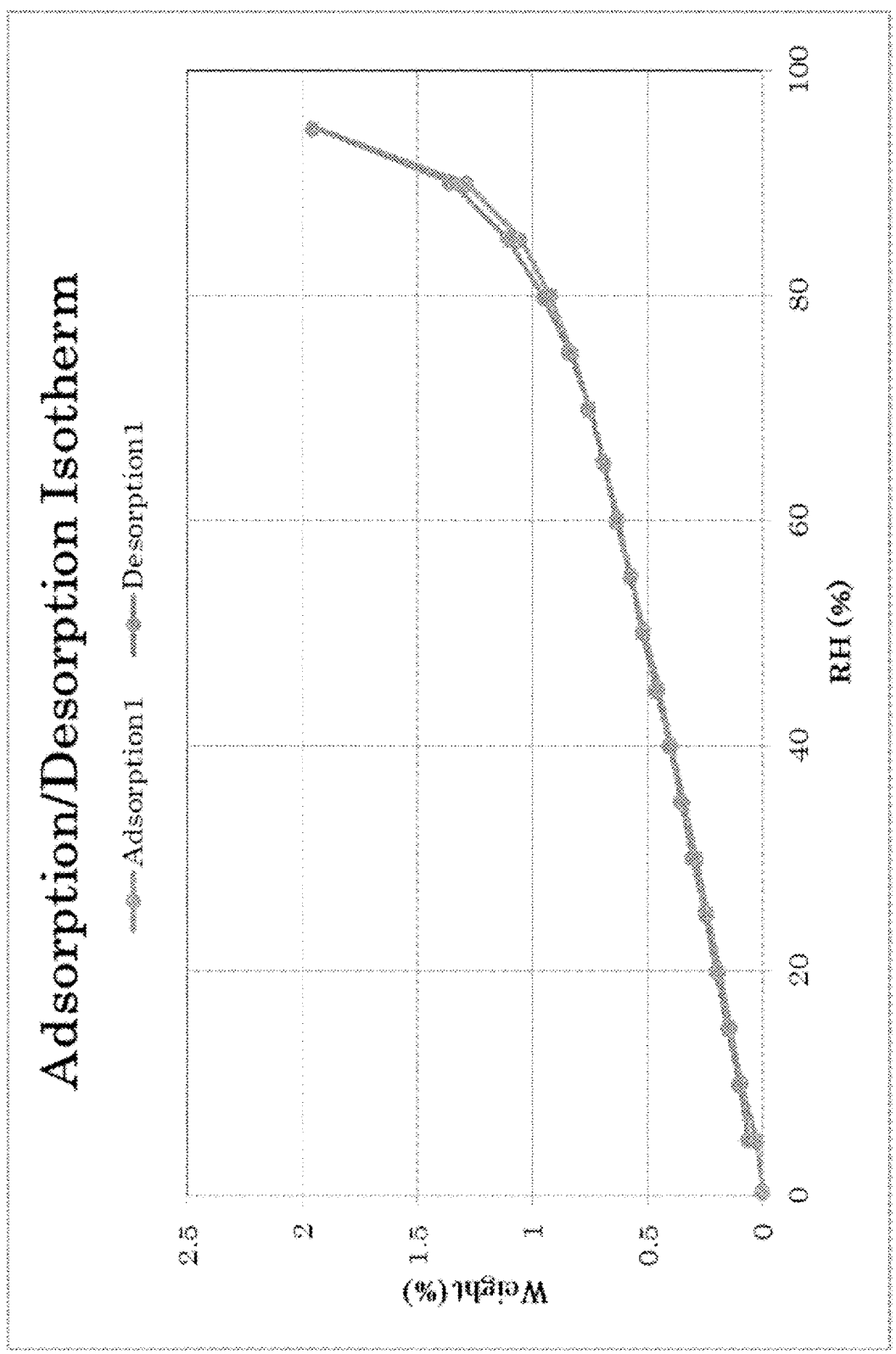
FIG. 9 is a moisture absorption/desorption isothermal curve of the succinic acid salt of Compound A. The axis of ordinates represents weight change ratio (%), and the axis of abscissas represents relative humidity (% RH).

Powder X-ray diffraction, differential scanning calorie (DSC) measurement and moisture absorption/desorption test were carried out with respect to the obtained crystal FIG. 7 is powder X-ray diffraction spectrum of the crystal of the succinic acid salt of Compound A. FIG. 8 is a differential scanning calorie (DSC) curve of the crystal of the succinic acid salt of Compound A.

In FIG. 7, the crystal of the succinic acid salt of Compound A had characteristic peaks at diffraction angles (2θ±0.2°) of 6.3°, 12.4°, 18.0°, 21.1°, 22.2° and 24.8 in the powder X-ray diffraction spectrum.

In FIG. 8, the crystal has a peak temperature in a differential scanning calorie (DSC) curve with an endothermic peak in the vicinity of 164° C.

Production Example 5: Synthesis of a Crystal of a
L-Tartaric Acid Salt of Compound A 165 mg of L-tartaric acid and 25 mL of methanol were added to 500 mg of the Compound A obtained according to the method of Production Example 1. The suspension was stirred for approximately 100 minutes at 50° C., for approximately 100 minutes at 40° C. and for approximately 19 hours and half at 25° C. in this order, filtered, and the solid was collected and dried to yield 166 mg of the titled crystal (yield: 25%).

Figure 10:
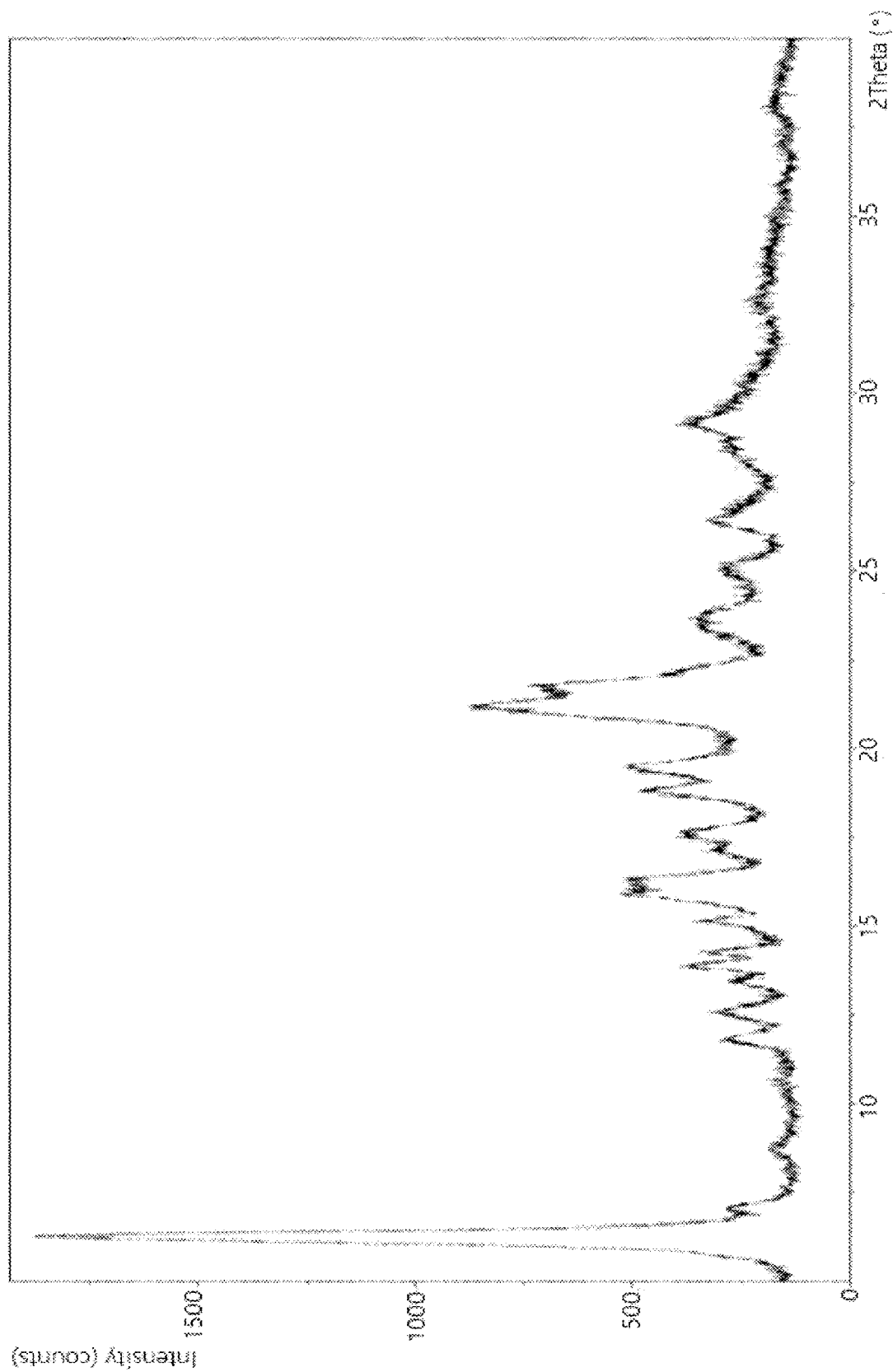
FIG. 10 is powder X-ray diffraction spectrum of a L-tartaric acid salt of Compound A. The axis of ordinates represents intensity (counts), and the axis of abscissas represents diffraction angle (2θ)).
Figure 11:
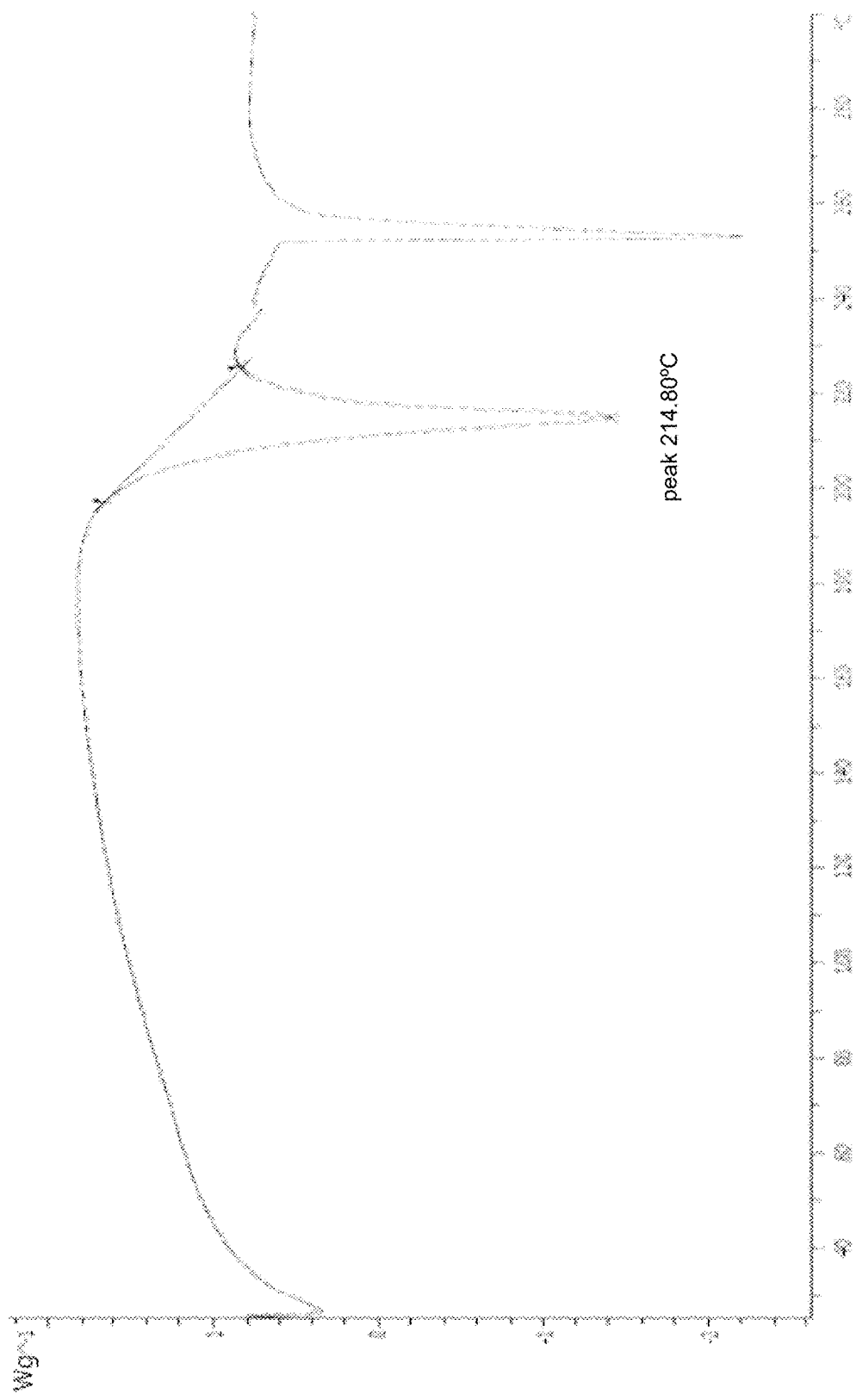
FIG. 11 is a differential scanning calorie (DSC) curve of the L-tartaric acid salt of Compound A. The axis of ordinates represents DSC (W/g), and the axis of abscissas represents temperature (° C.).
Figure 12:
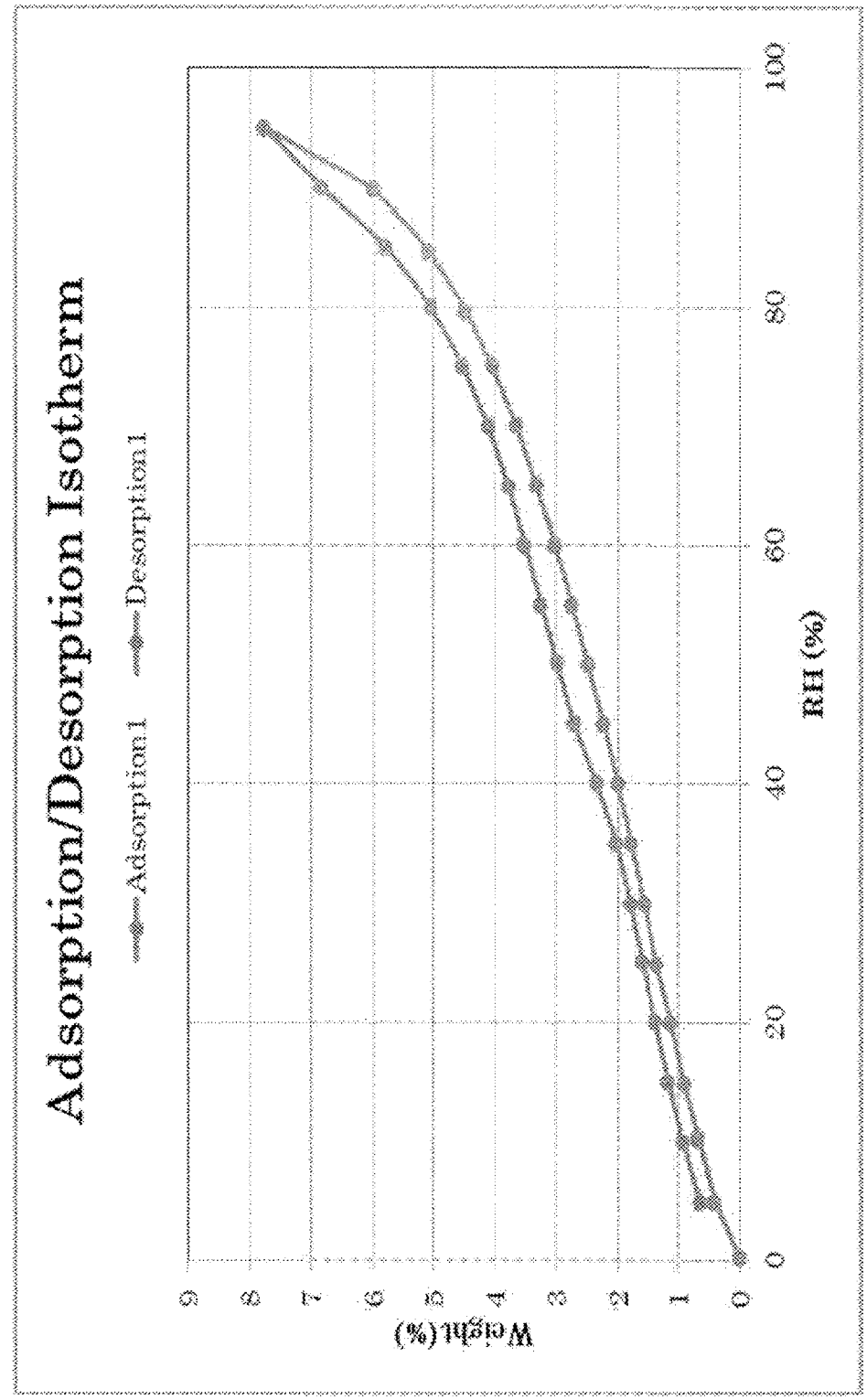
FIG. 12 is a moisture absorption/desorption isothermal curve of the L-tartaric acid salt of Compound A. The axis of ordinates represents weight change ratio (%), and the axis of abscissas represents relative humidity (% RH).

Powder X-ray diffraction, differential scanning calorie (DSC) measurement and moisture absorption/desorption test were carried out with respect to the obtained crystal FIG. 10 is powder X-ray diffraction spectrum of the crystal of the L-tartaric acid salt of Compound A. FIG. 11 is a differential scanning calorie (DSC) curve of the crystal of the L-tartaric acid salt of Compound A.

In FIG. 10, the crystal of the succinic acid salt of Compound A had characteristic peaks at diffraction angles (2θ±0.2°) of 6.3°, 11.8°, 12.6°, 18.8° and 19.6° in the powder X-ray diffraction spectrum.

In FIG. 11, the crystal has a peak temperature in a differential scanning calorie (DSC) curve with an endothermic peak in the vicinity of 215° C.

Production Example 6: Synthesis of a Crystal of a
Sorbic Acid Salt of Compound A 70.5 mg of sorbic acid and 7.5 mL of ethyl acetate were added to 300 mg of the Compound A obtained according to the method of Production Example 1. The suspension was stirred for approximately 90 minutes at 50° C., filtered, and the solid was collected and dried to yield 167 mg of the titled crystal (yield: 45%).

Powder X-ray diffraction, differential scanning calorie (DSC) measurement and moisture absorption/desorption test were carried out with respect to the obtained crystal FIG. 13 is powder X-ray diffraction spectrum of the crystal of the sorbic acid salt of Compound A. FIG. 14 is a differential scanning calorie (DSC) curve of the crystal of the sorbic acid salt of Compound A.

In FIG. 13, the crystal of the sorbic acid salt of Compound A had characteristic peaks at diffraction angles (2θ±0.2°) of 5.5°, 10.9°, 16.2°, 17.2°, 20.3° and 24.4° in the powder X-ray diffraction spectrum.

In FIG. 14, the crystal has a peak temperature in a differential scanning calorie (DSC) curve with an endothermic peak in the vicinity of 147° C.

Test Example 1

Moisture Absorption/Desorption Test

Moisture absorption/desorption test was carried out on the following test conditions. A dedicated quartz holder was filled with about 10 mg of sample, and a weight of the sample at each humidity was measured and recorded in a continuous manner under the following conditions. Handling of the devices including data processing was based on the method and the process indicated in each device.

Device: VTI SA+ (manufactured by TA Instruments Inc.)
Drying temperature: 60° C.
Temperature rising speed: 1° C./min.
Equilibrium in drying: It is confirmed that no reduction of 0.01 wt % occurs in 5 minutes, in a range not exceeding 300 minutes.
Temperature for measurement: 25° C.
Equilibrium in humidification: It is confirmed that no increase of 0.01 wt % occurs in 5 minutes, in a range not exceeding 120 minutes.
Relative humidity program: Raised by 5% RH from 5% RH to 95% RH, and lowered by 5% RH from 95% RH to 5% RH.

FIG. 3, FIG. 6, FIG. 9, FIG. 12 and FIG. 15 are moisture absorption/desorption isothermal curves of the crystal of the benzoic acid salt of Compound A produced in Product Example 2, the free form of Compound A produced in Product Example 3, the succinic acid salt of Compound A produced in Product Example 4, the L-tartaric acid salt of Compound A produced in Product Example 5 and the sorbic acid salt of Compound A produced in Product Example 6, respectively.

Figure 6:
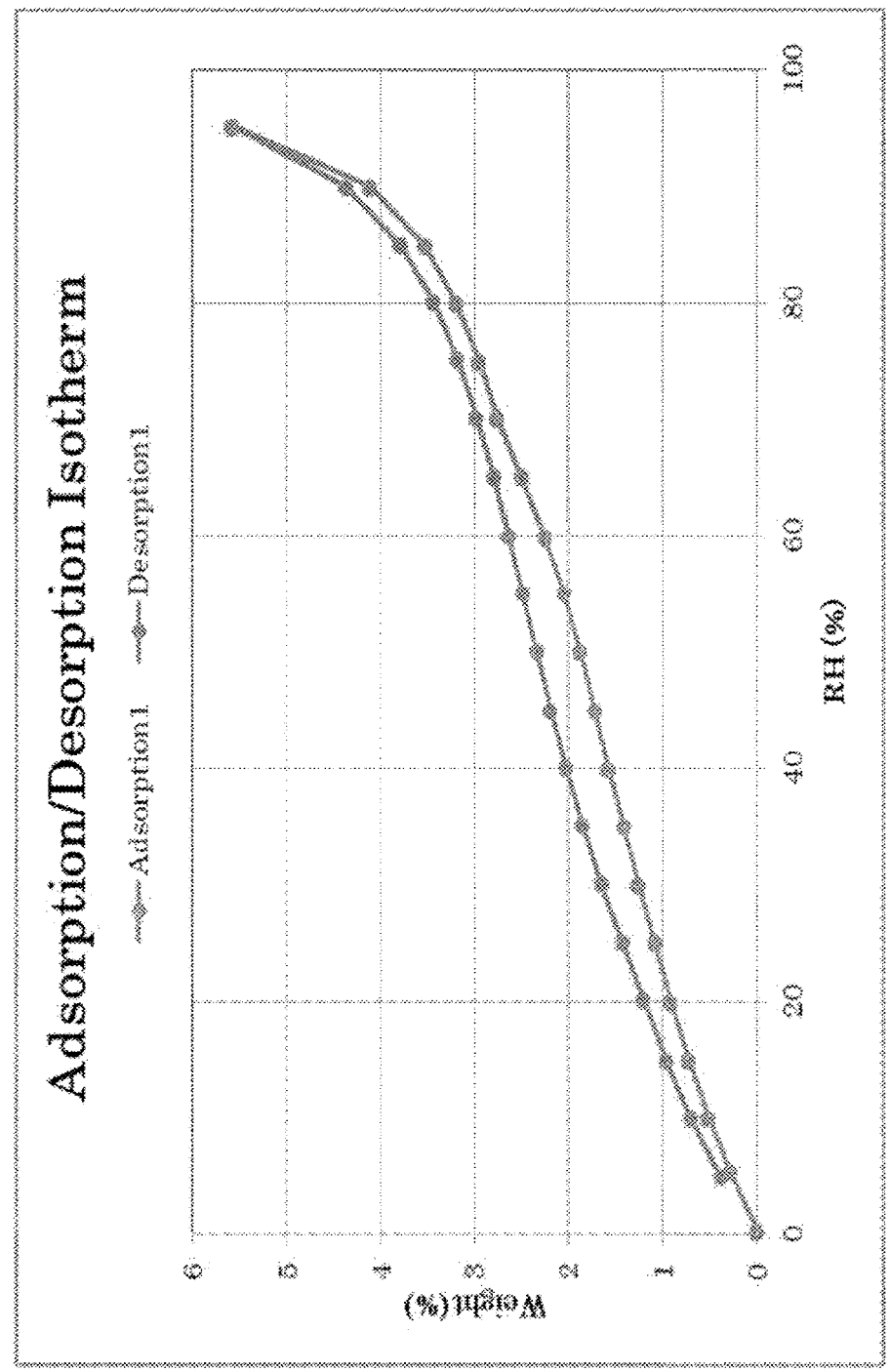
FIG. 6 is a moisture absorption/desorption isothermal curve of the free form Form C of Compound A. The axis of ordinates represents weight change ratio (%), and the axis of abscissas represents relative humidity (% RH).

As can be seen in FIG. 6, when the free form of Compound A was humidified at a relative humidity of from 5 to 95% which is within the range of the measurement condition, the weight change thereof was about +5.6% w/w at a maximum. When the humidity was lowered from the relative humidity of 95%, Compound A almost returned to the original condition. That is, it was found that the free form of Compound A had the characteristic of channel hydrate which would absorb/desorb moisture depending on humidity.

In contrast, the weight change of the benzoic acid salt of Compound A was +0.7% w/w at maximum. The weight change of the sorbic acid salt of Compound A was +1.9% w/w at maximum. Both of which returned to the original condition when a humidity was lowered. Thus, it was confirmed that the benzoic acid salt of Compound A and the sorbic acid salt of Compound A are less adsorptive and/or disorptive of moisture, reducing the characteristic of channel hydrate.

The weight change of the L-tartaric acid salt of Compound A was +7.8% w/w.

Test Example 2

Solid Stability Test (Accelerated Test)

Solid stability was measured under the following conditions, with respect to the benzoic acid salt of Compound A, the free form of Compound A, the sucinic acid salt of Compound A and the sorbic acid salt of Compound A obtained in Product Examples 2 to 4 and 6, when they were stored for 4 weeks at 60° C./ambient humidity (sealed condition).

Storage amount: about 25 to 50 mg Storage container: Brown glass container

Method of preparing sample solution: Sample was dissolved in 50% acetonitrile such that a concentration of the sample would be 0.5 mg/mL.

Mass of analogous substance in the sample solution was measured by HPLC analysis. Handling of the devices including data processing was based on the method and the process indicated in each device. (Device: Shimadzu Corporation Prominence-i) The analogous substance refers to one or more substances that are detected other than the starting substance (Compound A or the salt thereof) in each sample solution.

Column: Zorbax Eclipse Plus C18 (4.6×150 mm, 3.5 m, manufactured by Agilent technology)
UV detection: 220 nm
Column temperature: 40° C.
Column flow rate: 1.0 mL/min
Amount of injection: 5 μL
Temperature of sample cooler: 5° C.
Concentration of sample: 0.5 mg/mL
Mobile phase A: 10 mmol/L phosphate buffer (pH 6.5): Acetonitrile mixed solution (9:1)
Mobile phase B: Acetonitrile
Gradient: The mixture ratio of the mobile phase A and the mobile phase B was adjusted as in TABLE 1.

TABLE 1

| Time (min) | Mobile phase A (vol %) | Mobile phase B (vol %) |
|---|---|---|
| 0-8.5 | 90 to 55 | 10 to 45 |
| 8.5-15.5 | 55 to 50 | 45 to 50 |
| 15.5-23 | 50 to 33 | 50 to 67 |

TABLE 1-continued

| Time (min) | Mobile phase A (vol %) | Mobile phase B (vol %) |
|---|---|---|
| 23-34 | 33 | 67 |
| 34-35 | 33 to 90 | 67 to 10 |
| 35-45 | 90 | 10 |

TABLE 2 shows the results of evaluation on the measured mass of analogous substance before the storage and 4 weeks after the storage at 60° C. on sealed condition.

TABLE 2

| | Before storage (X) % | 4 weeks after storage at 60° C. on sealed condition (Y) % | Variation (Y) − (X) % |
|---|---|---|---|
| Purity of benzoic acid salt of Compound A (%) | 97.93 | 98.06 | +0.13 |
| Total mass of analogous substance of benzoic acid salt of Compound A (%) | 2.07 | 1.94 | −0.13 |
| Purity of free form of Compound A (%) | 98.52 | 98.15 | −0.37 |
| Total mass of analogous substance of free form of Compound A (%) | 1.48 | 1.85 | +0.37 |
| Purity of succinic acid salt of Compound A (%) | 97.01 | 96.09 | −0.92 |
| Total mass of analogous substance of succinic acid salt of Compound A (%) | 2.99 | 3.91 | +0.92 |
| Purity of sorbic acid salt of Compound A (%) | 98.63 | 97.99 | −0.64 |
| Total mass of analogous substance of sorbic acid salt of Compound A (%) | 1.37 | 2.01 | +0.64 |

Surprisingly, it was found that purity of benzoic acid salt of Compound A was maintained high compared to the other samples and almost no analogous substance was generated. It was confirmed that the benzoic acid salt of Compound A especially exhibits an excellent solid stability.

Test Example 3

In Phanrmacokinetic (PK) studies in rats, AUC, $C_{max}$(μM) and $T_{max}$(hr) of each of the three drugs, i.e., free form of Compound A, the benzoic acid salt of Compound A and the sorbic acid salts of Compound A, were calculated. Each drug was administered to the animal at at a dose of 32 mg/5 mL/kg. AUC of the free form of Compound A, the benzoic acid salt of Compound A and the sorbic acid salts of Compound A were 16.04 μM hr, 16.13 μM hr and 11.64 μM hr. $C_{max}$ of the three compounds were 2.56 μM, 2.68 μM and 2.03 μM. $T_{max}$ of the three compounds were 4.0 hr, 2.7 hr, and 2.3. It was revealed that the excellent drug adsorption was achieved even in the salt form.

The invention claimed is:

1. A crystalline form of a benzoic acid salt of 4-[5-[(3S)-3-aminopyrrolidine-1-carbonyl]-2-[2-fluoro-4-(2-hydroxy-2-methyl-propyl)phenyl]phenyl]-2-fluoro-benzonitrile, wherein the crystalline form is characterized by a powder X-ray diffraction pattern comprising diffraction peaks at 20 values of 15.3°±0.2°, 16.2°±0.2°, 17.8°±0.2°, 21.4°±0.2°, and 25.5°±0.2°.

2. A crystalline form of a benzoic acid salt of 4-[5-[(3S)-3-aminopyrrolidine-1-carbonyl]-2-[2-fluoro-4-(2-hydroxy-2-methyl-propyl)phenyl]phenyl]-2-fluoro-benzonitrile, wherein the crystalline form is characterized by a differential scanning calorimetry (DSC) curve with an endothermic peak in the range from 188° C. to 198° C.

3. The crystalline form according to claim 1, wherein the crystalline form is characterized by a powder X-ray diffraction pattern of FIG. 1.

4. A crystalline form of a sorbic acid salt of 4-[5-[(3S)-3-aminopyrrolidine-1-carbonyl]-2-[2-fluoro-4-(2-hydroxy-2-methyl-propyl)phenyl]phenyl]-2-fluoro-benzonitrile, wherein the crystalline form is characterized by a powder X-ray diffraction pattern comprising diffraction peaks at 2θ values of 5.5°±0.2°, 10.9°±0.2°, 16.2°±0.2°, 17.2°±0.2°, 20.3°±0.2°, and 24.4°±0.2°.

5. A crystalline form of a sorbic acid salt of 4-[5-[(3S)-3-aminopyrrolidine-1-carbonyl]-2-[2-fluoro-4-(2-hydroxy-2-methyl-propyl)phenyl]phenyl]-2-fluoro-benzonitrile, wherein the crystalline form is characterized by a differential scanning calorimetry (DSC) curve with an endothermic peak in the range from 142° C. to 152° C.

6. The crystalline form according to claim 4, wherein the crystalline form is characterized by a powder X-ray diffraction pattern of FIG. 13.

7. A pharmaceutical composition comprising the crystalline form according to claim 1.

8. The pharmaceutical composition according to claim 7, which is an orally administered composition.

9. A method of treating a malignant tumor in a patient in need thereof, the method comprising administering an effective amount of the crystalline form according to claim 1 to the patient.

10. A pharmaceutical composition comprising the crystalline form according to claim 4.

11. A method of treating a malignant tumor in a patient in need thereof, the method comprising administering an effective amount of the crystalline form according to claim 4 to the patient.

* * * * *